(12) United States Patent
Kato et al.

(10) Patent No.: US 8,414,491 B2
(45) Date of Patent: Apr. 9, 2013

(54) ULTRASONOGRAPH AND ULTRASONOGRAPH CONTROL METHOD

(75) Inventors: Makoto Kato, Kanagawa (JP); Hisashi Hagiwara, Kanagawa (JP); Kazuhiro Sunagawa, Miyagi (JP); Yoshinao Tannaka, Kanagawa (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 11/572,726

(22) PCT Filed: Jul. 27, 2005

(86) PCT No.: PCT/JP2005/013718
§ 371 (c)(1),
(2), (4) Date: Jan. 26, 2007

(87) PCT Pub. No.: WO2006/011504
PCT Pub. Date: Feb. 2, 2006

(65) Prior Publication Data
US 2008/0021318 A1    Jan. 24, 2008

(30) Foreign Application Priority Data

Jul. 28, 2004  (JP) .................. 2004-219753
Sep. 3, 2004   (JP) .................. 2004-257227
Jul. 27, 2005  (JP) .................. 2005-216640

(51) Int. Cl.
*A61B 8/00*    (2006.01)
(52) U.S. Cl. .......... 600/438; 600/407; 600/437
(58) Field of Classification Search .......... 600/437, 600/438, 440–447, 449–452, 458–464
See application file for complete search history.

(56) References Cited

U.S. PATENT DOCUMENTS

| 5,297,552 | A |   | 3/1994  | Mignot |
| 5,840,028 | A |   | 11/1998 | Chubachi et al. |
| 6,132,380 | A | * | 10/2000 | Cohen et al. .......... 600/481 |
| 6,749,571 | B2 | * | 6/2004 | Varghese et al. .......... 600/450 |

(Continued)

FOREIGN PATENT DOCUMENTS

| EP | 0 534 217 | 3/1993 |
| EP | 1 273 267 | 1/2003 |

(Continued)

OTHER PUBLICATIONS

European Search Report for corresponding Application No. 05767036.6 dated Nov. 23, 2007.

(Continued)

*Primary Examiner* — Tse Chen
*Assistant Examiner* — Mark Remaly
(74) *Attorney, Agent, or Firm* — Renner, Otto, Boisselle & Sklar, LLP

(57) ABSTRACT

An ultrasonic diagnostic apparatus includes: a positional displacement calculating section for calculating the magnitudes of positional displacements at multiple measuring points within a body tissue; a thickness variation calculating section for calculating thicknesses or thickness variations, each measured between two arbitrary points within the tissue set with respect to the measuring points, based on the magnitudes of positional displacements; and a maximum/minimum value calculating section for finding the maximum and minimum thicknesses or thickness variations during a maximum value finding period and a minimum value finding period. At least one of the greatest thickness difference, strain and elastic property is calculated based on a difference between the maximum and minimum thicknesses or thickness variations.

37 Claims, 21 Drawing Sheets

U.S. PATENT DOCUMENTS

| | | |
|---|---|---|
| 2003/0013962 A1 | 1/2003 | Bjaerum et al. |
| 2003/0149365 A1* | 8/2003 | Torp et al. ............. 600/450 |
| 2006/0173309 A1* | 8/2006 | Suzuki et al. ........... 600/437 |

FOREIGN PATENT DOCUMENTS

| | | |
|---|---|---|
| JP | 62-266040 | 11/1987 |
| JP | 05-168633 | 7/1993 |
| JP | 10-005226 | 1/1998 |
| JP | 2000-229078 | 8/2000 |
| JP | 2002-209857 | 7/2002 |
| JP | 2004-159672 | 6/2004 |

OTHER PUBLICATIONS

International Search Report for corresponding Application No. PCT/JP2005/013718 mailed Sep. 20, 2005.

Hiroshi Kanai et al.; "Elasticity Imaging of Atheroma with Transcutaneous Ultrasound Preliminary Study"; Circulation, vol. 107, 2003, pp. 3018-3021. (Cited in [0011], p. 5 of the description).

* cited by examiner

ULTRASONOGRAPH AND ULTRASONOGRAPH CONTROL METHOD

TECHNICAL FIELD

The present invention relates to an ultrasonic diagnostic apparatus. More particularly, the present invention relates to an ultrasonic diagnostic apparatus for measuring the attribute property of a tissue in an organism and also relates to a method for controlling such an ultrasonic diagnostic apparatus.

BACKGROUND ART

Recently, the number of people suffering from various circulatory system diseases, including heart infarction and brain infarction, has been on the rise, thus making it more and more urgent to prevent and treat these diseases.

The pathopoiesis of heart or brain infarction is closely correlated to arterial sclerosis. More specifically, if an atheroma is created on the arterial wall or if no arterial cells are produced anymore due to various factors such as elevated blood pressure, then the artery loses its elasticity to become hard and fragile. Also, if the blood vessel is clogged up where the atheroma has been created or if a vascular tissue covering the atheroma has ruptured, then the atheroma will move itself into the blood vessel to clog up the artery elsewhere or to rupture the hardened portions of the artery. As a result, these diseases are caused. That is why it is important to diagnose the arterial sclerosis as early as possible to prevent or treat these diseases.

In the prior art, the lesion of arterial sclerosis is diagnosed by directly observing the inside of the blood vessel with a vascular catheter. However, this diagnosis needs to be carried out with a vascular catheter inserted into the blood vessel of a testee, thus imposing a heavy load on him or her. For that reason, the vascular catheter observation is usually adopted to locate the lesion of arterial sclerosis in a patient who is already known to suffer from that disease but has never been used to make a medical checkup on a supposedly healthy person.

A checkup may be easily made without imposing excessively heavy load on a testee if the index of cholesterol, which is one of major causes of arterial sclerosis, or the blood pressure is measured. However, neither of these values directly indicates the degree of advancement of arterial sclerosis.

Also, if the arterial sclerosis can be diagnosed early enough to administer some medicine to its patient, then the disease can be treated effectively. However, it is said that once the arterial sclerosis has advanced to a certain degree, the farther advancement of that disease can be checked with the administration of medicine but it is difficult to repair the hardened artery completely.

That is why a method or apparatus for determining the degree of advancement of arterial sclerosis at an early stage of that disease without imposing too much load on a testee is now in high demand.

Meanwhile, an ultrasonic diagnostic apparatus or an X-ray diagnostic apparatus has been used in the prior art as a non-invasive medical apparatus that imposes only a light load on a person under test. Specifically, by irradiating the testee with an ultrasonic wave or an x-ray that has been produced externally, shape information or information about the variation in the shape of his or her internal body with time can be acquired without causing pain to him or her. When the information about the variation with time (i.e., mobility information) in the shape of an object under test in his or her body can be obtained, the attribute information of the object can be obtained. That is to say, the vascular elastic property of the organism can be known and the degree of advancement of the arterial sclerosis can be detected directly.

Among other things, the ultrasonic diagnosis is superior to the X-ray diagnosis because the ultrasonic diagnosis can be made just by putting an ultrasonic probe on a person under test. That is to say, in the ultrasonic diagnosis, there is no need to administer a contrast medium to the person under test and there is no concern about potential X-ray exposure, either.

Recently, however, some ultrasonic diagnostic apparatuses can have significantly improved measuring accuracy thanks to remarkable advancement of electronic technologies. As a result, ultrasonic diagnostic apparatuses for measuring the very small motion of a vital tissue have been developed. For example, Patent Document No. 1 discloses a technique of tracking an object of measurement highly accurately by analyzing the amplitude and phase of an ultrasonic echo signal by a restricted minimum square method. This technique is called a "phase difference tracking method". According to this technique, vibration components of a vascular motion, having an amplitude of several micrometers and a frequency of as high as several hundreds of Hz, can be measured accurately. Thus, it was reported that the thickness variation or strain of the vascular wall could be measured highly accurately on the order of several microns.

By adopting such a high-accuracy measuring technique, the two-dimensional distribution of the elastic property of the arterial wall can be plotted in detail. For example, Non-Patent Document No. 1 shows an example of presenting the two-dimensional distribution of the elasticity of the iliac bone arterial vascular wall as an image superposed on a B-mode tomogram.

It is known that the hardness of the arterial wall is not uniform but has some distribution. That is why in diagnosing the arterial sclerosis, it is important to know the exact hardness distribution of the arterial wall. According to the method disclosed in Non-Patent Document No. 1, the elasticity, which is a characteristic quantity showing the degree of advancement of the arterial sclerosis, is presented two-dimensionally, and therefore, the hardened portion of the arterial wall can be located accurately.

Patent Document No. 1: Japanese Patent Application Laid-Open Publication No. 10-5226
 Non-Patent Document No. 1: Hiroshi Kanai et al., "Elasticity Imaging of Atheroma with Transcutaneous Ultrasound Preliminary Study", Circulation, Vol. 107, pp. 3018-3021, 2003

DISCLOSURE OF INVENTION

Problems to be Solved by the Invention

However, since the measurements can now be done on the order of several micrometers thanks to the techniques disclosed in Patent Document No. 1 and Non-Patent Document No. 1, for example, the influence of noise is increasing. In addition, the ultrasonic diagnosis is supposed to be carried out by putting an ultrasonic probe on the measuring spot of a person under test. That is why if the person under test moved during the measurement, the probe could no longer be located right over the measuring spot.

In that case, an ultrasonic reflected wave could not be obtained properly from the vital tissue of the person under test. Then, the measurements could not be done as intended or the measured values might be affected by noise and become inaccurate. In addition, if such inaccurate results of measurements could not be judged inaccurate, then the inaccurate results of measurements would be taken for accurate ones by mistake. As a result, the diagnosis that has been made based on the results of measurements might be inappropriate or the reliability of the diagnosis might decrease.

In order to overcome at least one of the problems described above, an object of the present invention is to provide an ultrasonic diagnostic apparatus that can make accurate and highly reliable measurements and a method of controlling such an ultrasonic diagnostic apparatus.

Means for Solving the Problems

An ultrasonic diagnostic apparatus according to the present invention includes: a transmitting section for driving an ultrasonic probe that sends out an ultrasonic transmitted wave toward a tissue of an organism; a receiving section for receiving an ultrasonic reflected wave through the ultrasonic probe to generate a received signal, the ultrasonic reflected wave being produced by getting the ultrasonic transmitted wave reflected by the tissue of the organism; a phase detecting section for detecting the phase of the received signal to generate a phase detected signal; a positional displacement calculating section for calculating the magnitudes of positional displacements at multiple measuring points, which have been set on the tissue of the organism, based on the phase detected signal; a thickness variation calculating section for calculating thicknesses or thickness variations based on the magnitudes of positional displacements, each said thickness or each said thickness variation being measured between two arbitrary points, which have been set with respect to the multiple measuring points; and a maximum/minimum value calculating section for finding the maximum and minimum thicknesses or the maximum and minimum thickness variations during a maximum value finding period and a minimum value finding period, which are defined as respective partial periods of one cardiac cycle of the organism. At least one of the greatest thickness difference, strain and elastic property is calculated based on either a difference between the maximum and minimum thicknesses or a difference between the maximum and minimum thickness variations.

In one preferred embodiment, the ultrasonic diagnostic apparatus further includes an attribute property value calculating section that receives information about the maximum and minimum thicknesses or the maximum and minimum thickness variations and information about a blood pressure value of the organism and that figures out an elastic property based on either the difference between the maximum and minimum thicknesses or the difference between the maximum and minimum thickness variations and on the blood pressure value.

In another preferred embodiment, the maximum value finding period and the minimum value finding period are set during the one cardiac cycle of the organism so as not to overlap with each other.

In another preferred embodiment, at least one of the maximum value finding period and the minimum value finding period is set synchronously with a biomedical signal generated by the organism.

In this particular preferred embodiment, the biomedical signal is represented as an electrocardiogram by an electrocardiograph.

In a specific preferred embodiment, at least one of the maximum value finding period and the minimum value finding period is set based on at least one of P, Q, R, S, T and U waves of the electrocardiogram.

In an alternative preferred embodiment, the biomedical signal is represented as a phonocardiogram by a phonocardiograph.

In a specific preferred embodiment, at least one of the maximum value finding period and the minimum value finding period is set based on at least one of I, II, III and IV sounds of the phonocardiogram.

In still another preferred embodiment, the biomedical signal is a sphygmogram.

In this particular preferred embodiment, at least one of the maximum value finding period and the minimum value finding period is set based on at least one of S, P, T, C and D waves of the sphygmogram.

In yet another preferred embodiment, at least one of the maximum value finding period and the minimum value finding period is set based on a positional displacement waveform that has been figured out in advance by the positional displacement calculating section.

In yet another preferred embodiment, the thickness variation calculating section figures out in advance a thickness variation waveform, showing a variation in the thickness of the body tissue, according to the magnitude of positional displacement and at least one of the maximum value finding period and the minimum value finding period is set based on the thickness variation waveform.

In yet another preferred embodiment, the thickness variation calculating section figures out in advance a vascular caliber variation waveform, showing a variation in the vascular caliber of the body tissue, according to the magnitude of positional displacement and at least one of the maximum value finding period and the minimum value finding period is set based on the vascular caliber variation waveform.

In yet another preferred embodiment, each of the maximum value finding period and the minimum value finding period has a length corresponding to 1% to 25% of one cardiac cycle.

In yet another preferred embodiment, the ultrasonic diagnostic apparatus further includes an accuracy checking section for checking the accuracy of at least one of the greatest thickness difference, the strain and the elastic property based on a result of comparison between the maximum and minimum thicknesses or between the maximum and minimum thickness variations.

In this particular preferred embodiment, if the maximum value is equal to or smaller than the minimum value, then the accuracy checking section judges the accuracy of at least one of the greatest thickness difference, the strain and the elastic property to be low.

In an alternative preferred embodiment, the ultrasonic diagnostic apparatus further includes an accuracy checking section for checking the accuracy of at least one of the greatest thickness difference, the strain and the elastic property based on a relation between a time when at least one of the maximum and minimum thicknesses or the maximum and minimum thickness variations is obtained and at least one of the associated maximum and minimum value finding periods.

In this particular preferred embodiment, if the time when at least one of the maximum and minimum thicknesses or the maximum and minimum thickness variations is obtained coincides with a start time or end time of its associated finding period, then the accuracy checking section judges the accuracy of at least one of the greatest thickness difference, the strain and the elastic property to be low.

In yet another preferred embodiment, the maximum/minimum value calculating section or the attribute property value calculating section sets at least one of the greatest thickness difference, the strain and the elastic property equal to a predetermined value according to the accuracy.

In yet another preferred embodiment, the accuracy checking section generates information showing the degree of the accuracy.

In yet another preferred embodiment, the ultrasonic diagnostic apparatus further includes a display section for presenting at least one of the greatest thickness difference, the strain and the elastic property.

In an alternative preferred embodiment, the ultrasonic diagnostic apparatus further includes a display section for presenting at least one of the greatest thickness difference, the strain and the elastic property, which is displayed two-dimensionally according to a position on the tissue of the organism in accordance with the information showing the degree of the accuracy.

In another alternative preferred embodiment, the ultrasonic diagnostic apparatus further includes a display section for presenting at least one of the greatest thickness difference, the strain and the elastic property and the accuracy, represented by the information showing the degree of the accuracy, as two-dimensional images reflecting the position on the tissue of the organism.

Another ultrasonic diagnostic apparatus according to the present invention includes: a transmitting section for driving an ultrasonic probe that sends out an ultrasonic transmitted wave toward a tissue of an organism; a receiving section for receiving an ultrasonic reflected wave through the ultrasonic probe to generate a received signal, the ultrasonic reflected wave being produced by getting the ultrasonic transmitted wave reflected by the tissue of the organism; a phase detecting section for detecting the phase of the received signal to generate a phase detected signal; a positional displacement calculating section for calculating the magnitudes of positional displacements at multiple measuring points, which have been set on the tissue of the organism, based on the phase detected signal; a thickness variation calculating section for calculating thicknesses or thickness variations based on the magnitudes of positional displacements, each said thickness or each said thickness variation being measured between two arbitrary points, which have been set with respect to the multiple measuring points; a maximum/minimum value calculating section for finding the maximum and minimum thicknesses or the maximum and minimum thickness variations; an attribute property value calculating section for figuring out at least one of the greatest thickness difference, strain and elastic property based on the difference between the maximum and minimum values; and an accuracy checking section for checking the accuracy of at least one of the greatest thickness difference, the strain and the elastic property by reference to times when the maximum and minimum values are obtained.

In one preferred embodiment, the ultrasonic diagnostic apparatus further includes an attribute property value calculating section that receives information about the maximum and minimum thicknesses or the maximum and minimum thickness variations and information about a blood pressure value of the organism and that figures out an elastic property based on either the difference between the maximum and minimum thicknesses or the difference between the maximum and minimum thickness variations and on the blood pressure value.

In another preferred embodiment, the accuracy checking section checks the accuracy by comparing the respective times when the maximum and minimum values are obtained with each other.

In another preferred embodiment, the maximum/minimum value calculating section finds the maximum and minimum values in a first period, which is equal to or shorter than one cardiac cycle of the organism.

In another preferred embodiment, the maximum/minimum value calculating section finds the maximum and minimum values in a first period, which is equal to or shorter than one cardiac cycle of the organism, and the accuracy checking section checks the accuracy by determining whether or not the time at which at least one of the maximum and minimum values is obtained falls within a second period, which is defined as a partial period of the first period during one cardiac cycle of the organism.

In this particular preferred embodiment, the first period is defined synchronously with a biomedical signal generated by the organism.

In another preferred embodiment, the biomedical signal is represented as an electrocardiogram by an electrocardiograph.

In a specific preferred embodiment, the first period is set based on at least one of P, Q, R, S, T and U waves of the electrocardiogram.

In an alternative preferred embodiment, the biomedical signal is represented as a phonocardiogram by a phonocardiograph.

In a specific preferred embodiment, the first period is set based on at least one of I, II, III and IV sounds of the phonocardiogram.

In still another preferred embodiment, the biomedical signal is a sphygmogram.

In this particular preferred embodiment, the first period is set based on at least one of S, P, T, C and D waves of the sphygmogram.

In yet another preferred embodiment, the first period is set based on a positional displacement waveform that has been figured out in advance by the positional displacement calculating section.

In yet another preferred embodiment, the thickness variation calculating section figures out in advance a thickness variation waveform, showing a variation in the thickness of the body tissue, according to the magnitude of positional displacement and the first period is set based on the thickness variation waveform.

In yet another preferred embodiment, the thickness variation calculating section figures out in advance a vascular caliber variation waveform, showing a variation in the vascular caliber of the body tissue, according to the magnitude of positional displacement and the first period is set based on the vascular caliber variation waveform.

In yet another preferred embodiment, the first period has a length corresponding to 5% to 75% of one cardiac cycle.

In yet another preferred embodiment, the maximum/minimum value calculating section or the attribute property value calculating section sets at least one of the greatest thickness difference, the strain and the elastic property equal to a predetermined value according to the accuracy.

In yet another preferred embodiment, the accuracy checking section generates information showing the degree of the accuracy.

In yet another preferred embodiment, the ultrasonic diagnostic apparatus further includes a display section for presenting at least one of the greatest thickness difference, the strain and the elastic property.

In an alternative preferred embodiment, the ultrasonic diagnostic apparatus further includes a display section for presenting at least one of the greatest thickness difference, the strain and the elastic property, which is displayed two-dimensionally according to a position on the tissue of the organism in accordance with the information showing the degree of the accuracy.

In another alternative preferred embodiment, the ultrasonic diagnostic apparatus further includes a display section for presenting at least one of the greatest thickness difference, the strain and the elastic property and the accuracy, represented by the information showing the degree of the accuracy, as two-dimensional images reflecting the position on the tissue of the organism.

Still another ultrasonic diagnostic apparatus according to the present invention includes: a transmitting section for driving an ultrasonic probe that sends out an ultrasonic transmitted wave toward a tissue of an organism; a receiving section for receiving an ultrasonic reflected wave through the ultrasonic probe to generate a received signal, the ultrasonic reflected wave being produced by getting the ultrasonic transmitted wave reflected by the tissue of the organism; a phase detecting section for detecting the phase of the received signal to generate a phase detected signal; a shape measured value calculating section for calculating the magnitudes of positional displacements at multiple measuring points, which have been set on the tissue of the organism, based on the phase detected signal and figuring out shape measured values based on the magnitudes of positional displacements, each said shape measured value being calculated between two arbitrary points, which have been set with respect to the multiple measuring points; an attribute property value calculating section for calculating attribute property values based on the shape measured values; a go/no-go testing section for determining whether or not each of the shape measured values and/or each of the attribute property values are/is correct value(s) and calculating a go/no-go ratio based the test results; and a display section for presenting the shape measured values and/or the attribute property values according to the go/non-go ratio.

In one preferred embodiment, if the go/no-go ratio and a predetermined threshold value satisfy a prescribed condition, the go/no-go testing section generates a presentation signal, indicating that the go/no-go ratio is good, and the display section presents a spatial distribution image of the shape measured values and/or the attribute property values in response to the presentation signal.

In another preferred embodiment, the attribute property value calculating section, the attribute property value calculating section and the go/no-go testing section perform their calculations every cardiac cycle of the organism and the display section continues to present the spatial distribution image of the shape measured values and/or the attribute property values until the next presentation signal is received.

In another preferred embodiment, the ultrasonic diagnostic apparatus further includes a storage section for storing the shape measured values and/or the attribute property values if the go/no-go ratio and the predetermined threshold value satisfy the prescribed condition. In accordance with a predetermined instruction, the display section presents a spatial distribution image of the newest ones of the shape measured values and/or attribute property values that are stored in the storage section.

In another preferred embodiment, the ultrasonic diagnostic apparatus includes a storage section for storing the go/no-go ratio. The go/no-go testing section compares every go/no-go ratio calculated to the best go/no-go ratio that is stored in the storage section and generates a presentation signal if the go/no-go ratio is better than the best go/no-go ratio. In response to the presentation signal, the display section presents a spatial distribution image of the shape measured values and/or the attribute property values.

In another preferred embodiment, if the go/no-go ratio is better than the best ratio, then the storage section stores the shape measured values and/or the attribute property values. In accordance with a predetermined instruction, the display section presents a spatial distribution image of the shape measured values and/or the attribute property values, at which the best go/no-go ratio stored in the storage section is obtained.

In a specific preferred embodiment, each said shape measured value is the greatest thickness difference of the body tissue of the organism.

In another specific preferred embodiment, each said attribute property value is the strain and/or elastic property of the body tissue of the organism.

A method for getting an ultrasonic diagnostic apparatus controlled by a control section of the ultrasonic diagnostic apparatus according to the present invention includes the steps of: (A) sending out an ultrasonic transmitted wave and receiving an ultrasonic reflected wave through the ultrasonic probe to generate a received signal, the ultrasonic reflected wave being produced by getting the ultrasonic transmitted wave reflected by a tissue of an organism; (B) detecting the phase of the received signal to generate a phase detected signal; (C) calculating the magnitudes of positional displacements at multiple measuring points, which have been set on the tissue of the organism, based on the phase detected signal; (D) calculating thicknesses or thickness variations based on the magnitudes of positional displacements, each said thickness or each said thickness variation being measured between two arbitrary points that have been set with respect to the multiple measuring points; (E) finding either the maximum and minimum thicknesses or the maximum and minimum thickness variations during a maximum value finding period and a minimum value finding period, which are defined as respective partial periods of one cardiac cycle of the organism; and (F) calculating at least one of the greatest thickness difference, strain and elastic property based on either a difference between the maximum and minimum thicknesses or a difference between the maximum and minimum thickness variations.

In one preferred embodiment, the step (F) includes receiving information about the maximum and minimum thicknesses or the maximum and minimum thickness variations and information about a blood pressure value of the organism and figuring out an elastic property based on either the difference between the maximum and minimum thicknesses or the difference between the maximum and minimum thickness variations and on the blood pressure value.

In another preferred embodiment, the step (E) includes setting the maximum value finding period and the minimum value finding period during the one cardiac cycle of the organism such that the maximum and minimum value finding periods do not overlap with each other.

In still another preferred embodiment, the step (E) includes setting at least one of the maximum value finding period and the minimum value finding period synchronously with a biomedical signal generated by the organism.

In yet another preferred embodiment, the biomedical signal is represented as an electrocardiogram by an electrocardiograph.

In yet another preferred embodiment, the control method further includes the step (G1) of checking the accuracy of at least one of the greatest thickness difference, the strain and the elastic property based on a result of comparison between the maximum and minimum thicknesses or between the maximum and minimum thickness variations.

In yet another preferred embodiment, if the maximum value is equal to or smaller than the minimum value, then the step (G1) includes judging the accuracy of at least one of the greatest thickness difference, the strain and the elastic property to be low.

In yet another preferred embodiment, the control method further includes the step (G2) of checking the accuracy of at least one of the greatest thickness difference, the strain and the elastic property based on a relation between a time when at least one of the maximum and minimum thicknesses or the maximum and minimum thickness variations is obtained and at least one of the associated maximum and minimum value finding periods.

In yet another preferred embodiment, if the time when at least one of the maximum and minimum thicknesses or the maximum and minimum thickness variations is obtained coincides with a start time or end time of its associated finding period, then the step (G2) includes judging the accuracy of at least one of the greatest thickness difference, the strain and the elastic property to be low.

In yet another preferred embodiment, the control method further includes the step (H) of setting at least one of the greatest thickness difference, the strain and the elastic property equal to a predetermined value according to the accuracy.

In yet another preferred embodiment, the step (G2) includes generating information showing the degree of the accuracy.

In yet another preferred embodiment, the control method further includes the step (I1) of presenting at least one of the greatest thickness difference, the strain and the elastic property.

In yet another preferred embodiment, the control method further includes the step (I2) of presenting at least one of the greatest thickness difference, the strain and the elastic property, which is displayed two-dimensionally according to a position on the tissue of the organism in accordance with the information showing the degree of the accuracy.

In yet another preferred embodiment, the control method further includes the step (I3) of presenting at least one of the greatest thickness difference, the strain and the elastic property and the accuracy, represented by the information showing the degree of the accuracy, as two-dimensional images reflecting the position on the tissue of the organism.

Another method for getting an ultrasonic diagnostic apparatus controlled by a control section of the ultrasonic diagnostic apparatus according to the present invention includes the steps of: (A) sending out an ultrasonic transmitted wave and receiving an ultrasonic reflected wave through the ultrasonic probe to generate a received signal, the ultrasonic reflected wave being produced by getting the ultrasonic transmitted wave reflected by a tissue of an organism; (B) detecting the phase of the received signal to generate a phase detected signal; (C) calculating the magnitudes of positional displacements at multiple measuring points, which have been set on the tissue of the organism, based on the phase detected signal; (D) calculating thicknesses or thickness variations based on the magnitudes of positional displacements, each said thickness or each said thickness variation being measured between two arbitrary points that have been set with respect to the multiple measuring points; (F) finding the maximum and minimum thicknesses or the maximum and minimum thickness variations; (G) figuring out at least one of the greatest thickness difference, strain and elastic property based on the difference between the maximum and minimum values; and (I) checking the accuracy of at least one of the greatest thickness difference, the strain and the elastic property by reference to times when the maximum and minimum values are obtained.

In one preferred embodiment, the step (G) includes receiving information about the maximum and minimum thicknesses or the maximum and minimum thickness variations and information about a blood pressure value of the organism and figuring out an elastic property based on either the difference between the maximum and minimum thicknesses or the difference between the maximum and minimum thickness variations and on the blood pressure value.

In another preferred embodiment, the step (I) includes checking the accuracy by comparing the respective times when the maximum and minimum values are obtained with each other.

In another preferred embodiment, the step (F) includes finding the maximum and minimum values in a first period, which is equal to or shorter than one cardiac cycle of the organism.

In another preferred embodiment, the step (F) includes finding the maximum and minimum values in a first period, which is equal to or shorter than one cardiac cycle of the organism, and the step (I) includes checking the accuracy by determining whether or not the time at which at least one of the maximum and minimum values is obtained falls within a second period, which is defined as a partial period of the first period during one cardiac cycle of the organism.

In this particular preferred embodiment, the first period is defined synchronously with a biomedical signal generated by the organism.

In another preferred embodiment, the control method further includes the step (J) of setting at least one of the greatest thickness difference, the strain and the elastic property equal to a predetermined value according to the accuracy.

In yet another preferred embodiment, the step (I) includes generating information showing the degree of the accuracy.

In yet another preferred embodiment, the control method further includes the step (K2) of presenting at least one of the greatest thickness difference, the strain and the elastic property.

In an alternative preferred embodiment, the control method further includes the step (K1) of presenting at least one of the greatest thickness difference, the strain and the elastic property, which is displayed two-dimensionally according to a position on the tissue of the organism in accordance with the information showing the degree of the accuracy.

In another alternative preferred embodiment, the control method further includes the step (K3) of presenting at least one of the greatest thickness difference, the strain and the elastic property and the accuracy, represented by the information showing the degree of the accuracy, as two-dimensional images reflecting the position on the tissue of the organism.

Still another method for getting an ultrasonic diagnostic apparatus controlled by a control section of the ultrasonic diagnostic apparatus according to the present invention includes the steps of: (A) sending out an ultrasonic transmitted wave and receiving an ultrasonic reflected wave through the ultrasonic probe to generate a received signal, the ultrasonic reflected wave being produced by getting the ultrasonic transmitted wave reflected by a tissue of an organism; (B) detecting the phase of the received signal to generate a phase detected signal; (C) calculating the magnitudes of positional displacements at multiple measuring points, which have been set on the tissue of the organism, based on the phase detected signal; (D) figuring out shape measured values based on the magnitudes of positional displacement, each said shape measured value being calculated between two arbitrary points, which have been set with respect to the multiple measuring points; (E) calculating attribute property values based on the shape measured values; (F) determining whether each of the shape measured values and/or each of the attribute property values are/is correct value(s) and calculating a go/no-go ratio based the test results; and (G) presenting the shape measured values and/or the attribute property values according to the go/non-go ratio.

In one preferred embodiment, if the go/no-go ratio and a predetermined threshold value satisfy a prescribed condition, the step (F) includes generating a presentation signal, indicating that the go/no-go ratio is good, and the step (G) includes presenting a spatial distribution image of the shape measured values and/or the attribute property values in response to the presentation signal.

In another preferred embodiment, the steps (D), (E) and (F) include performing respective calculations every cardiac cycle of the organism and the step (G) includes continuing to present the spatial distribution image of the shape measured values and/or the attribute property values until the next presentation signal is received.

In another preferred embodiment, the control method further includes the step (H1) of storing the shape measured values and/or the attribute property values if the go/no-go ratio and the predetermined threshold value satisfy the prescribed condition. The step (G) includes presenting a spatial distribution image of the newest ones of the shape measured values and/or attribute property values that are stored in a storage section in accordance with a predetermined instruction.

In another preferred embodiment, the control method includes the step (H2) of storing the go/no-go ratio. The step (F) includes comparing every go/no-go ratio calculated to the best go/no-go ratio that is stored in the step (H2), and generating a presentation signal if the go/no-go ratio is better than the best go/no-go ratio. The step (G) includes presenting a spatial distribution image of the shape measured values and/or the attribute property values in response to the presentation signal.

In another preferred embodiment, the control method further includes the step (H3) of storing the shape measured values and/or the attribute property values if the go/no-go ratio is better than the best ratio. The step (G) includes presenting a spatial distribution image of the shape measured values and/or the attribute property values, at which the best go/no-go ratio stored in the storage section is obtained, in accordance with a predetermined instruction.

In a specific preferred embodiment, each said shape measured value is the greatest thickness difference of the body tissue of the organism.

In another specific preferred embodiment, each said attribute property value is the strain and/or elastic property of the body tissue of the organism.

Effects of the Invention

According to the present invention, the maximum and minimum values of thicknesses or thickness variations are found during a maximum value finding period and a minimum value finding period, which are defined as respective partial periods of one cardiac cycle. As a result, the unwanted effects of noise and other disturbances can be reduced in the remaining periods other than the maximum and minimum value finding periods and measurements can be done accurately.

In addition, the accuracy of the greatest thickness difference, strain or elastic property is checked at the points in time when the maximum and minimum values are obtained. Thus, by considering the degrees of accuracy of the measuring results, inaccurate measuring results are much less likely to be taken for accurate ones erroneously and high-reliability diagnosis can be made based on the measuring results.

On top of that, a go/no-go test is carried out to determine whether each shape measured value or attribute property value is a correct one or not, a go/no-go ratio is calculated based on the results of the go/no-go testing, and the shape measured and attribute property values are presented depending on the go/no-go ratio. Consequently, high-reliability diagnosis can be made based on the measuring results.

Figure 8:
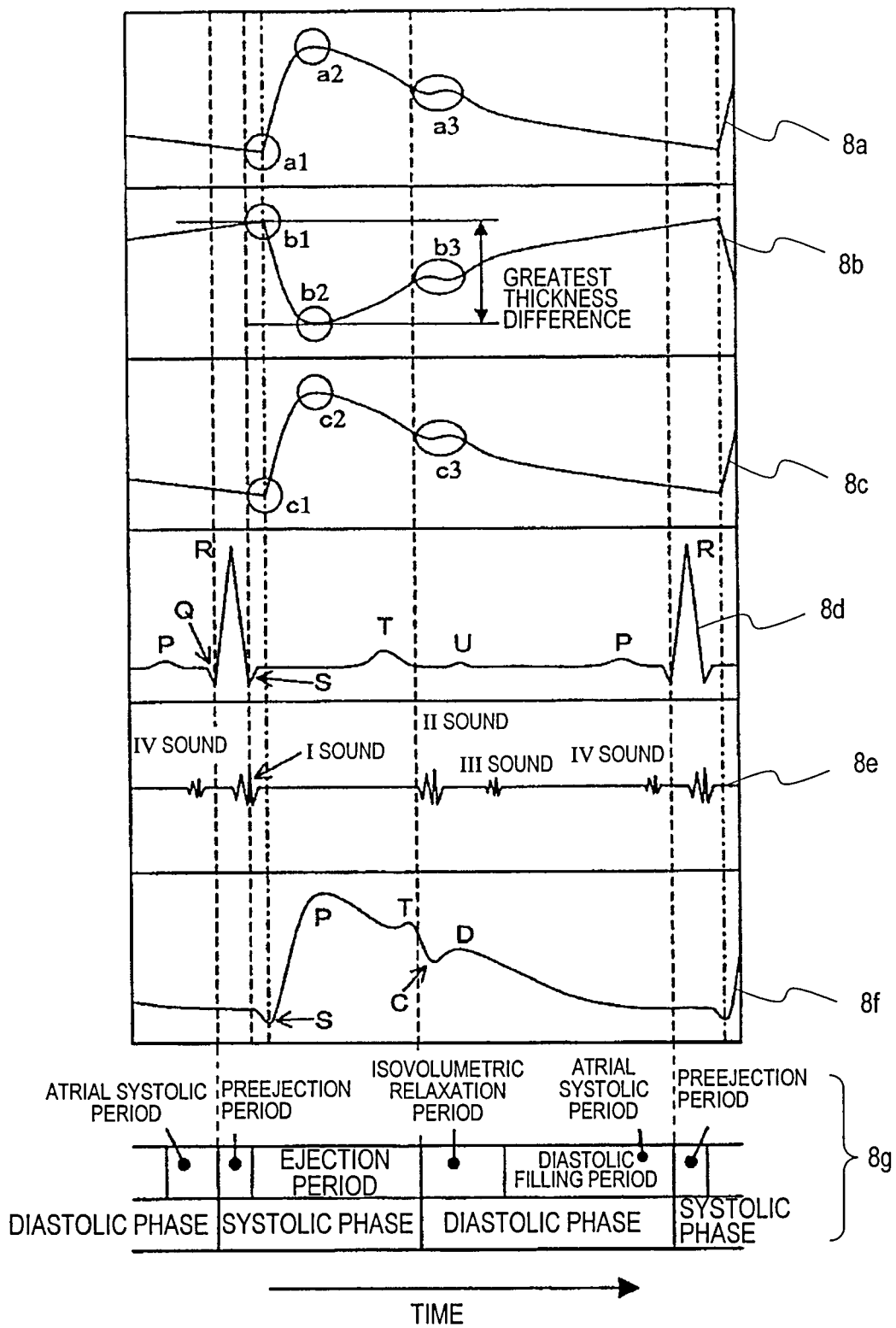

Graphs 8a, 8b and 8c of FIG. 8 show the magnitude of positional displacement, variation in thickness and variation in the inside diameter of the blood vessel as measured on a human carotid artery by the ultrasonic diagnostic apparatus of the present invention; graphs 8d, 8e and 8f of FIG. 8 show an electrocardiogram, a phonocardiogram and a pulse wave; and chart 8g of FIG. 8 shows phenomena occurring in one cardiac cycle.

Figure 9:
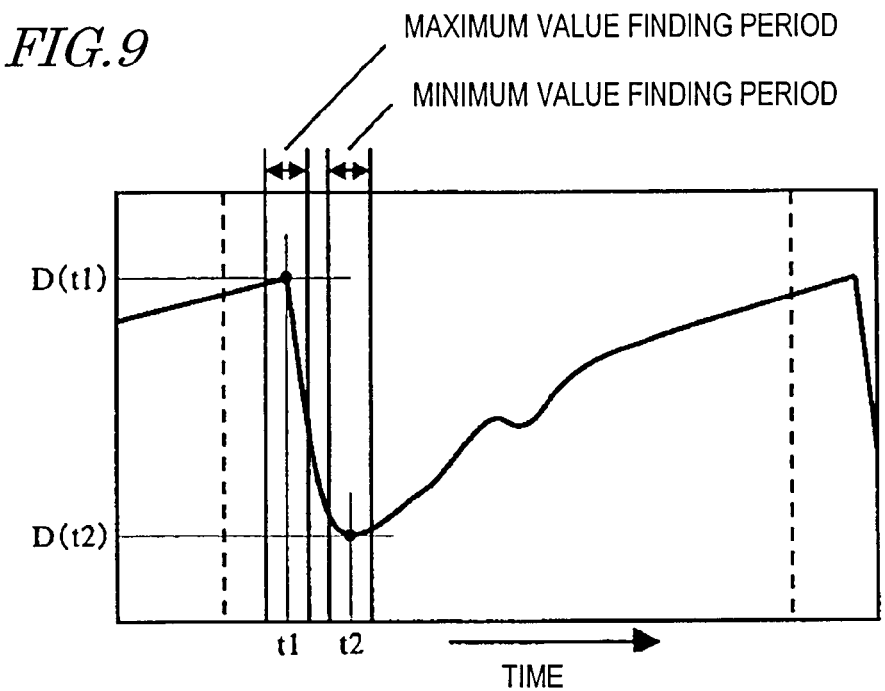

FIG. 9 shows an example in which a maximum value finding period and a minimum value finding period are defined within a part of a thickness variation waveform corresponding to one cardiac cycle.

Figure 10A:
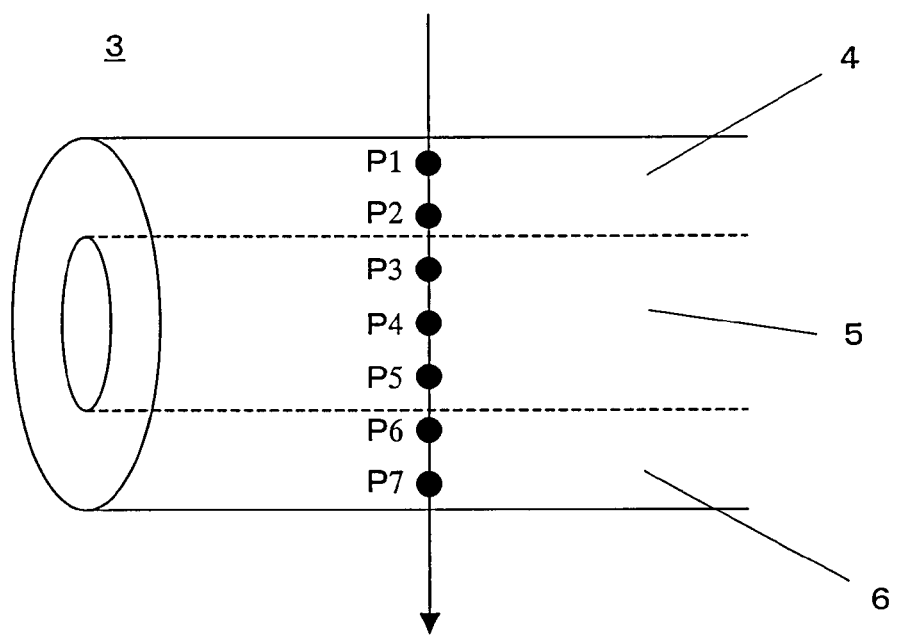

FIG. 10A is a side view schematically showing measuring points on an acoustic line of an ultrasonic beam propagating through a blood vessel.

Figure 10B:
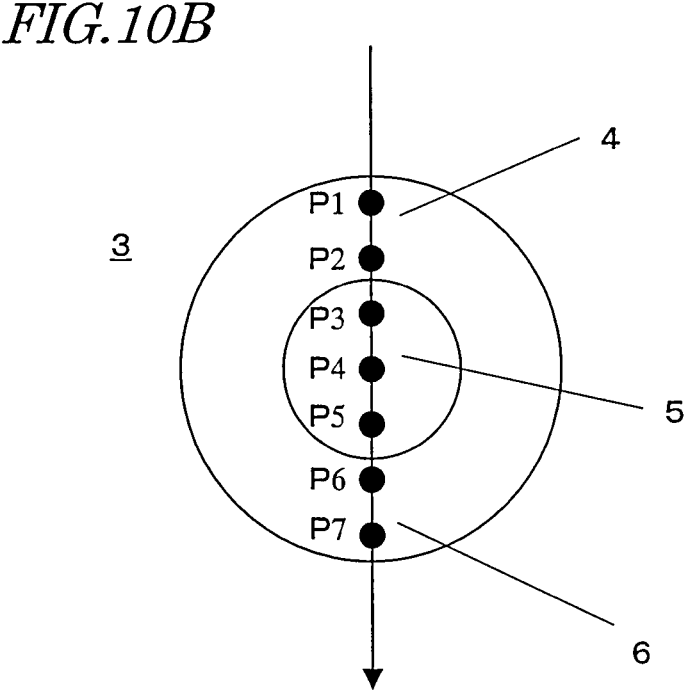

FIG. 10B is a cross-sectional view schematically showing the measuring points on the acoustic line of the ultrasonic beam propagating through the blood vessel.

Figure 11A:
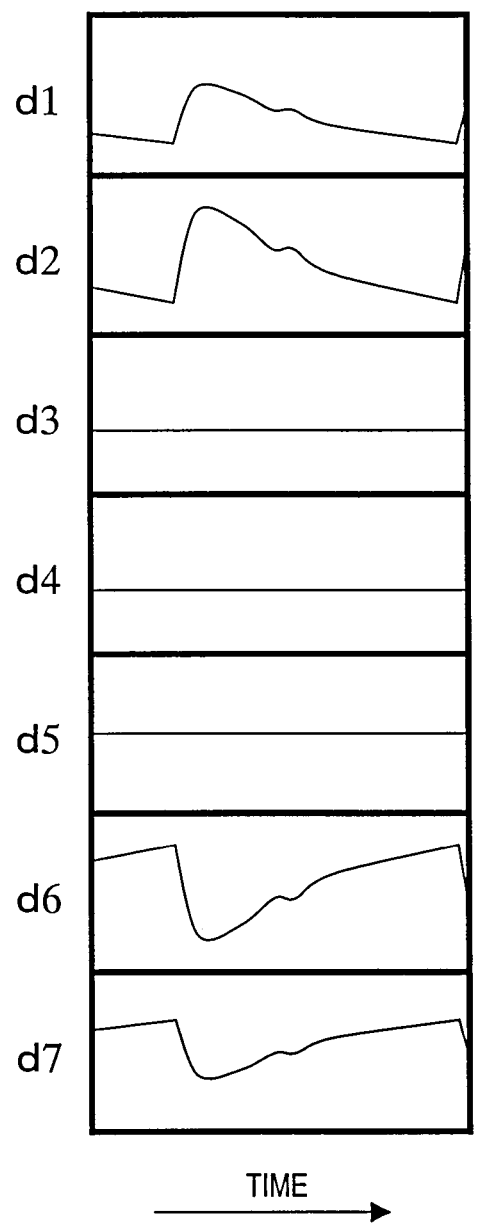

FIG. 11A is schematic graphs showing the magnitudes of positional displacements at the measuring points shown in FIGS. 10A and 10B.

Figure 11B:
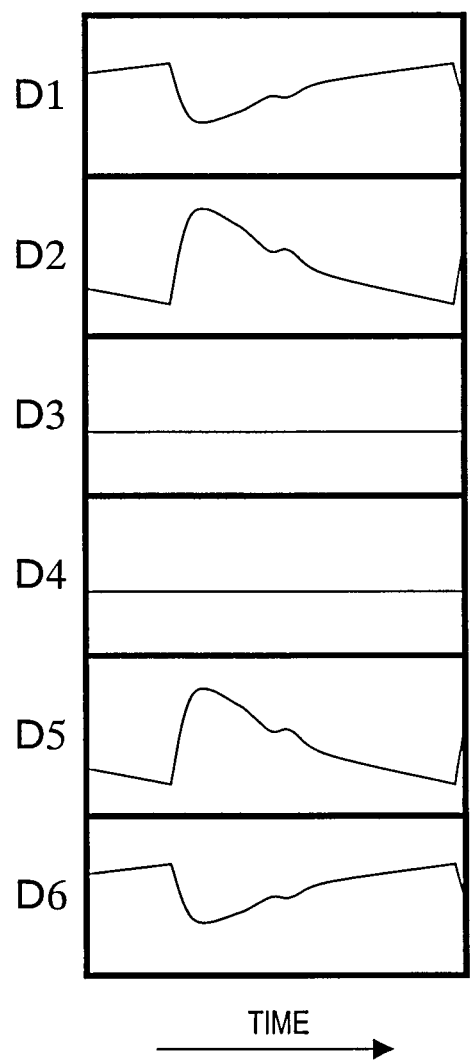

FIG. 11B is schematic graphs showing the thickness variations between two adjacent ones of the measuring points shown in FIGS. 10A and 10B.

Figure 12:
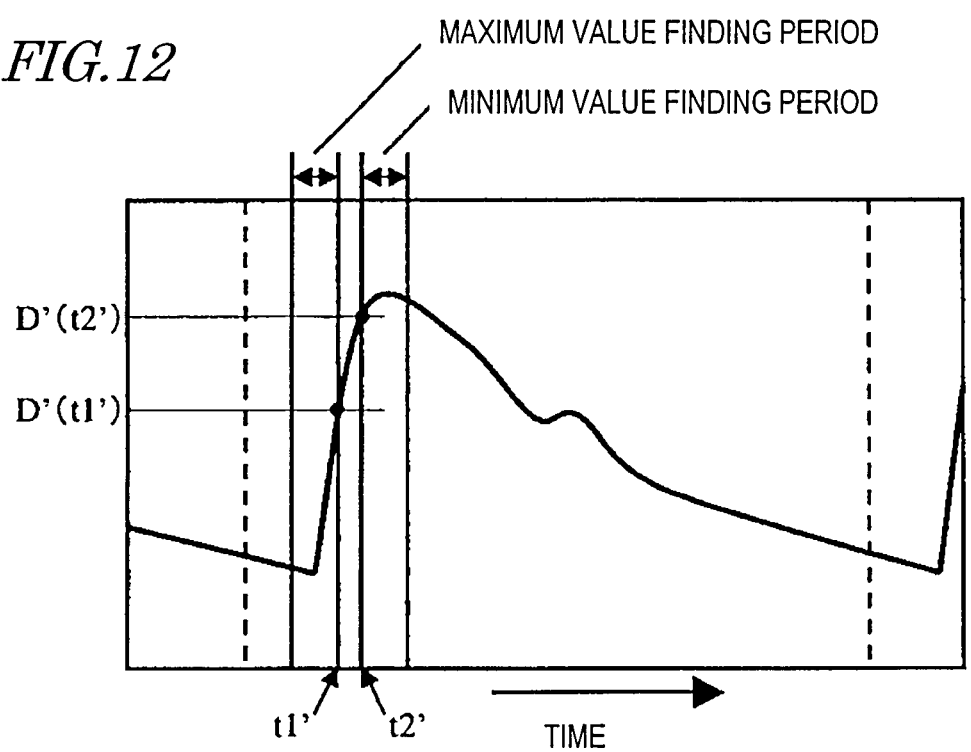

FIG. 12 shows another example of the maximum and minimum value finding periods that are set within a part of a thickness variation waveform corresponding to one cardiac cycle.

Figure 13A:
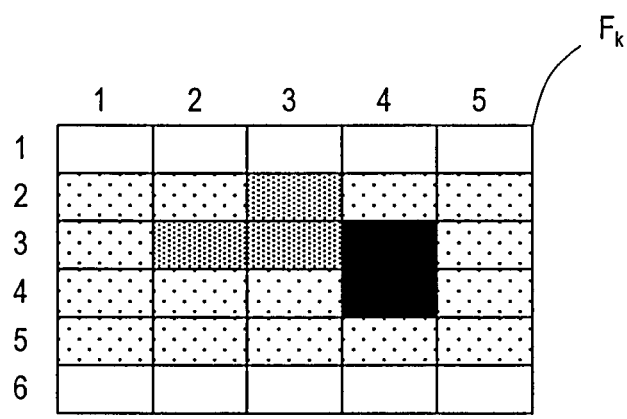

FIG. 13A schematically illustrates an exemplary two-dimensional elastic property image presented on a display section.

Figure 13B:
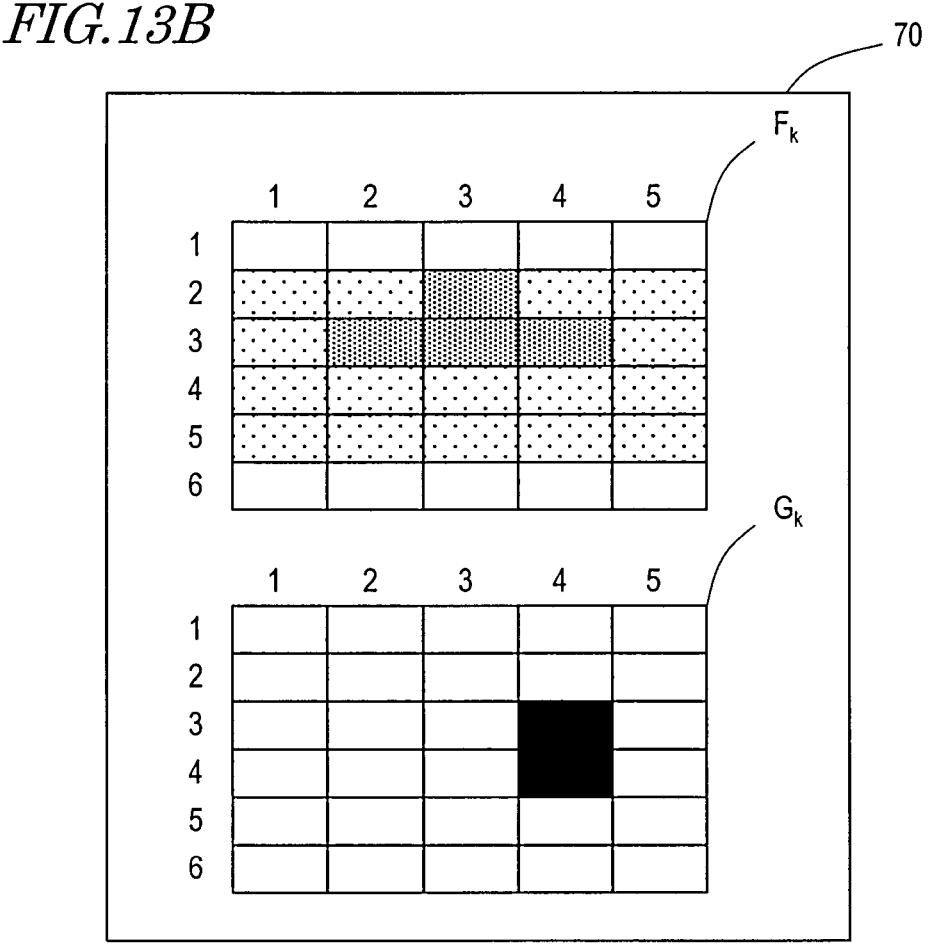

FIG. 13B schematically illustrates another exemplary two-dimensional elastic property image presented on the display section.

Figure 14:
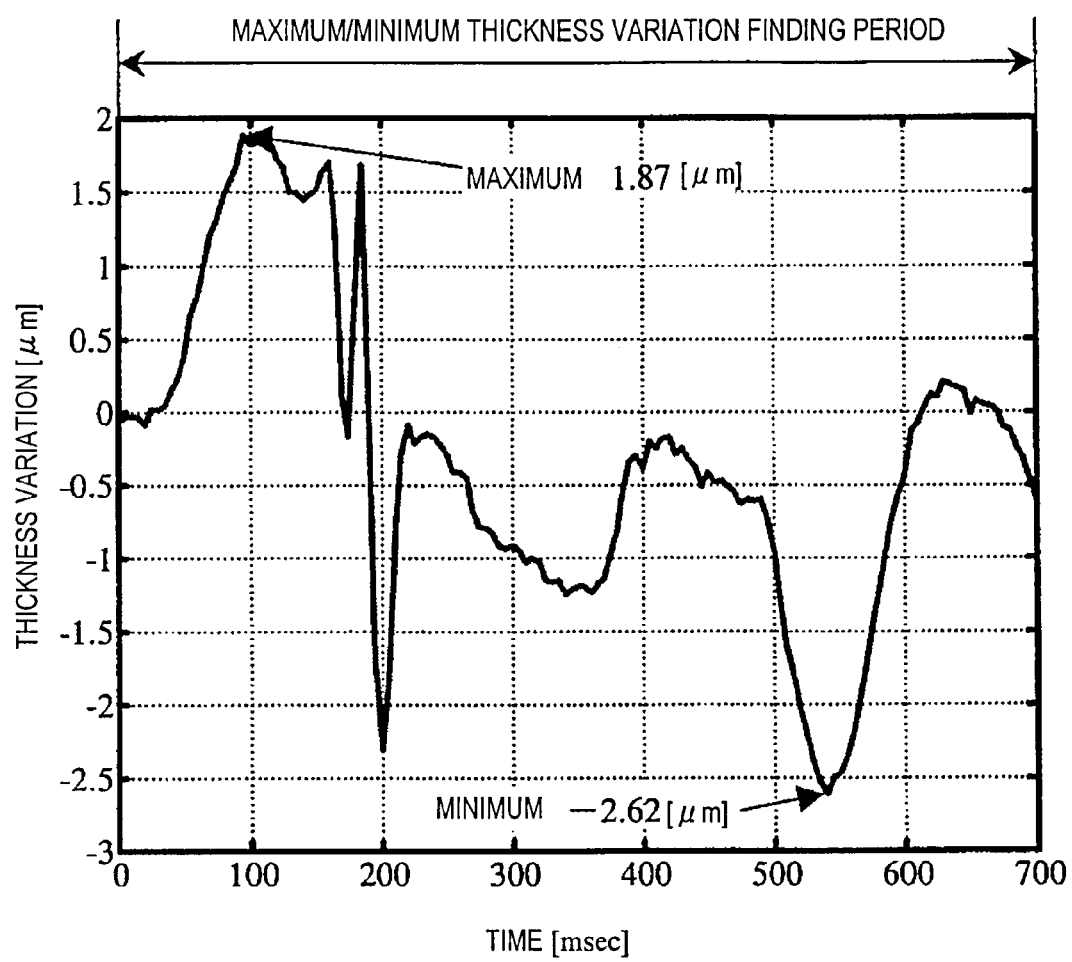

FIG. 14 is a graph showing a variation with time in the thickness of the anterior wall of a human carotid artery, which was measured with the ultrasonic diagnostic apparatus of the first preferred embodiment.

Figure 15:
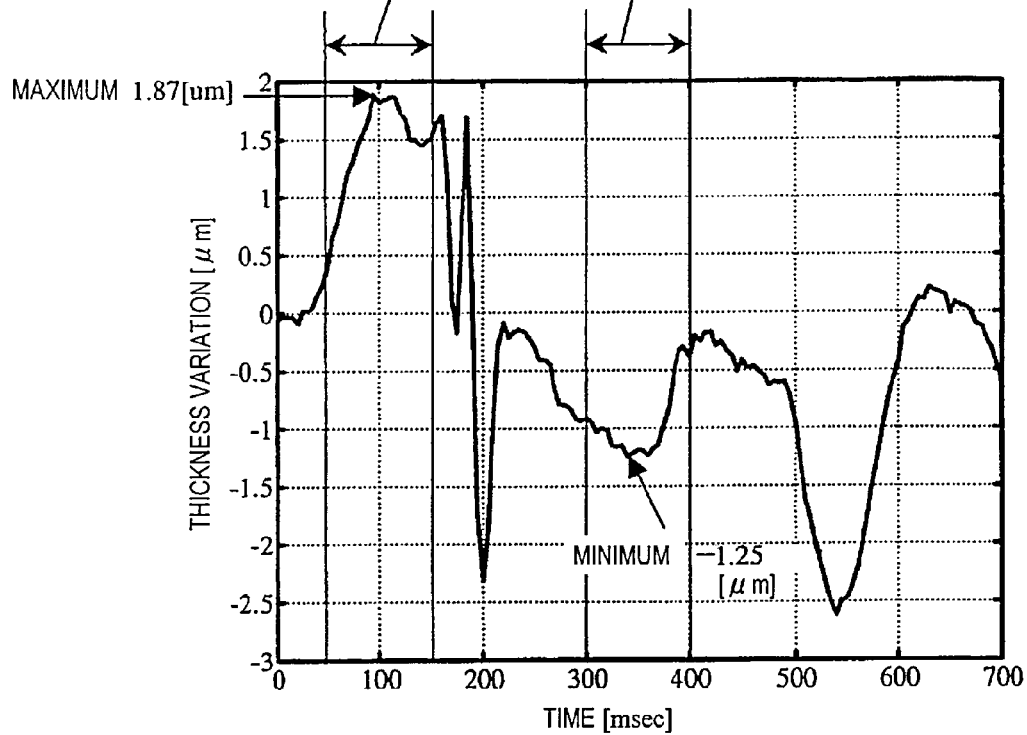

FIG. 15 is a graph showing a variation with time in the thickness of the anterior wall of the same human carotid artery that was measured with the ultrasonic diagnostic apparatus of the first preferred embodiment and also showing the maximum and minimum value finding periods defined.

Figure 16:
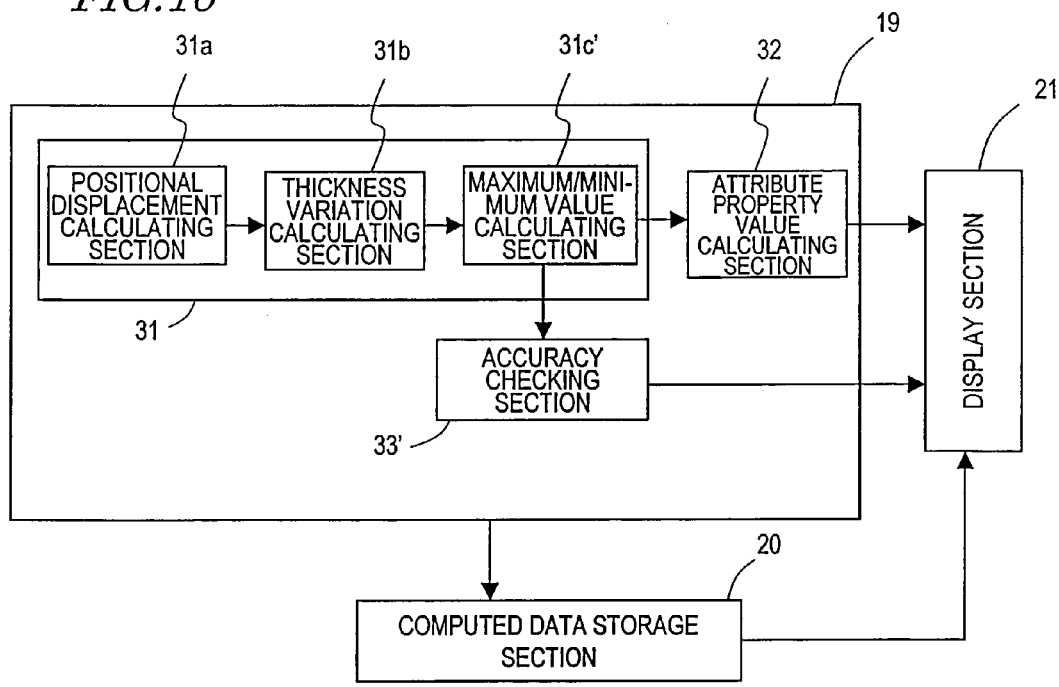

FIG. 16 is a block diagram showing the configuration of core sections of an ultrasonic diagnostic apparatus according to a second preferred embodiment of the present invention.

Figure 17:
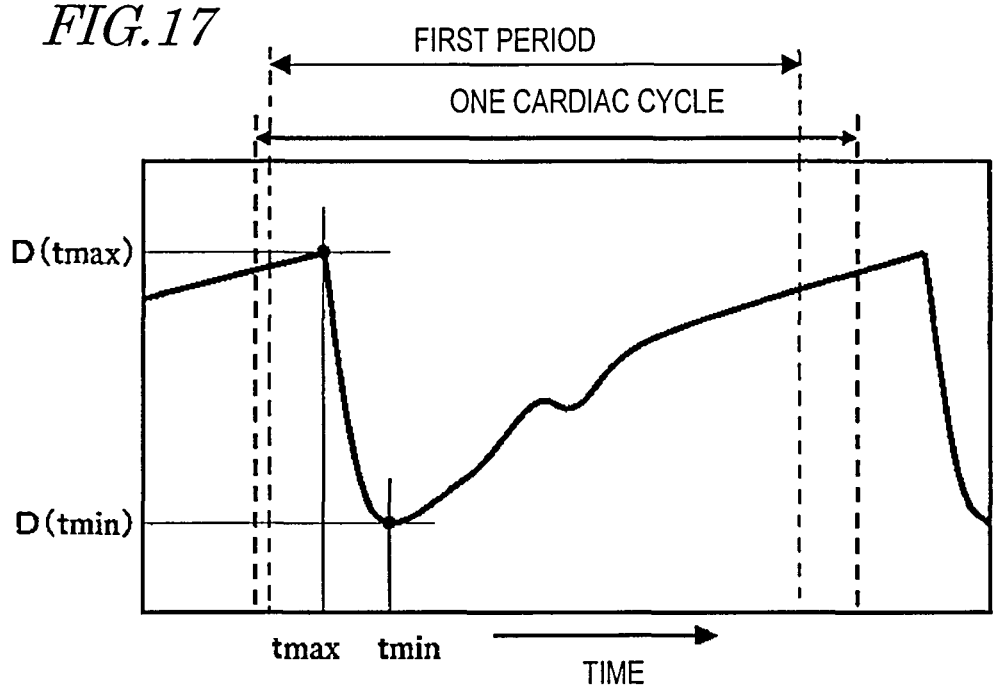

FIG. 17 is a graph showing how to set a maximum and minimum value finding period for a thickness variation waveform.

Figure 18:
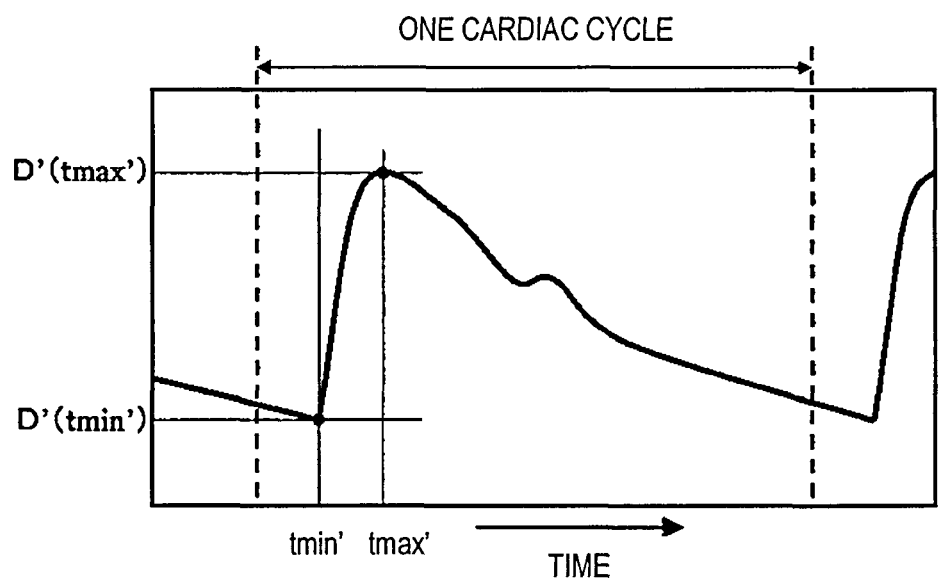

FIG. 18 is a graph showing the maximum and minimum values of a thickness variation waveform with inverted positive and negative values.

Figure 19:
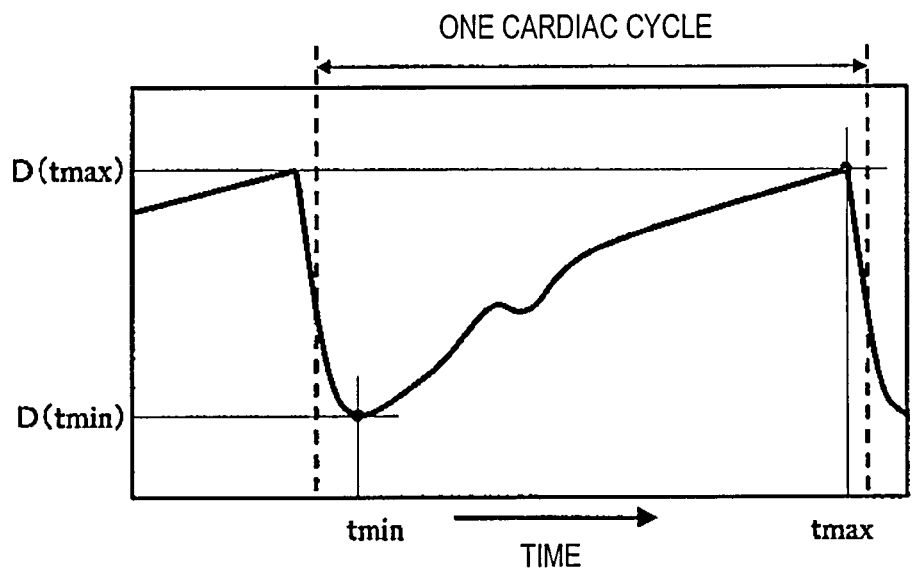

FIG. 19 is a graph showing where the maximum and minimum values of the thickness variation waveform are located if one cardiac cycle begins at a different time.

Figure 20:
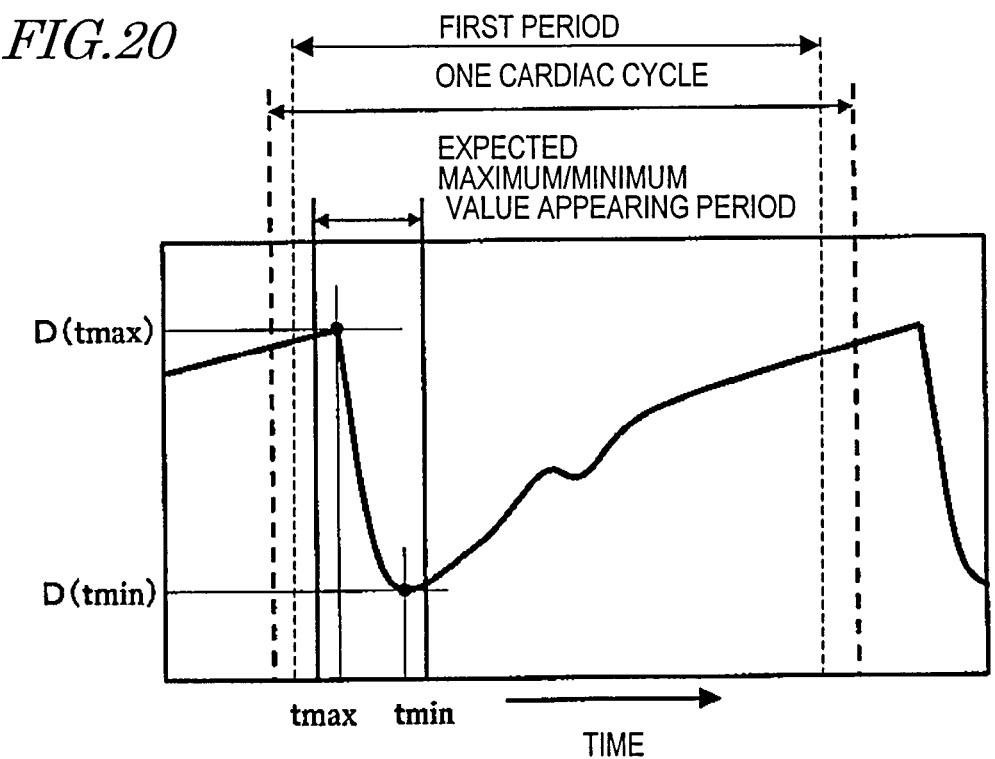

FIG. 20 is a graph showing a maximum/minimum value finding period and an expected maximum/minimum value appearing period that are defined for a thickness variation waveform.

Figure 21:
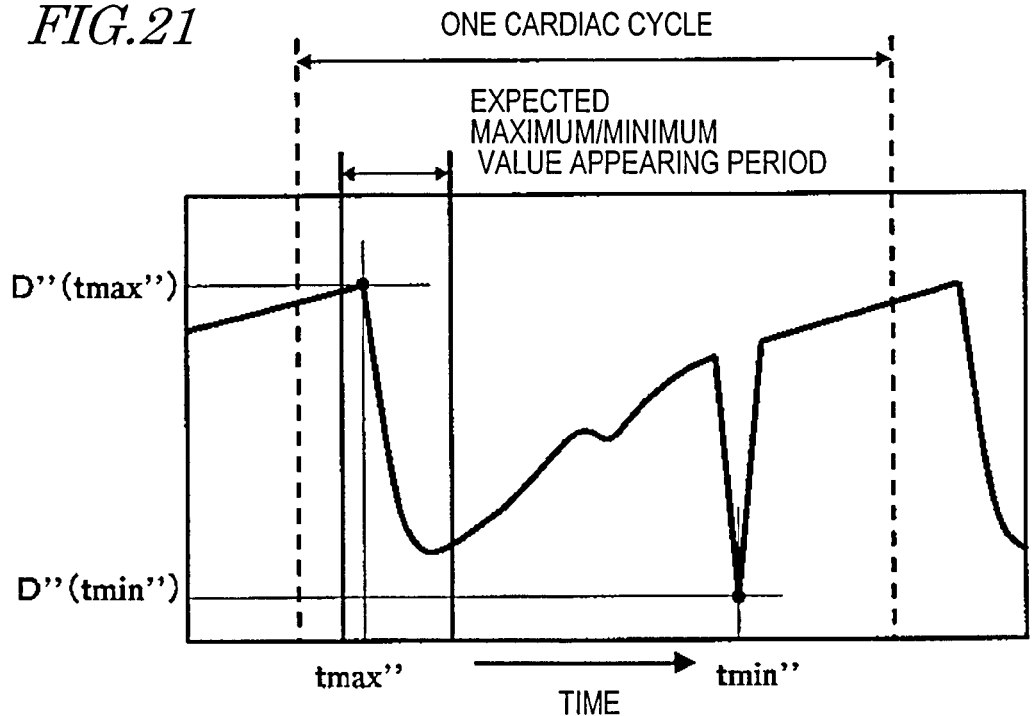

FIG. 21 is a graph showing another maximum/minimum value finding period and another expected maximum/minimum value appearing period that are defined for a thickness variation waveform.

Figure 22:
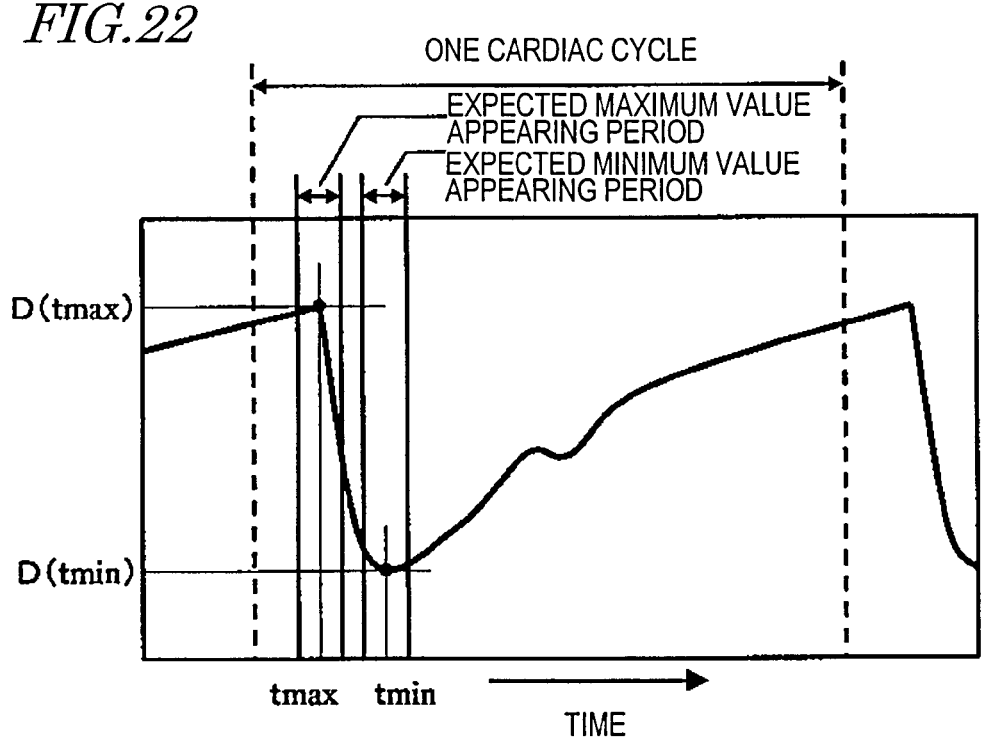

FIG. 22 is a graph showing a maximum/minimum value finding period, an expected maximum value appearing period and an expected minimum value appearing period that are defined for a thickness variation waveform.

Figure 23:
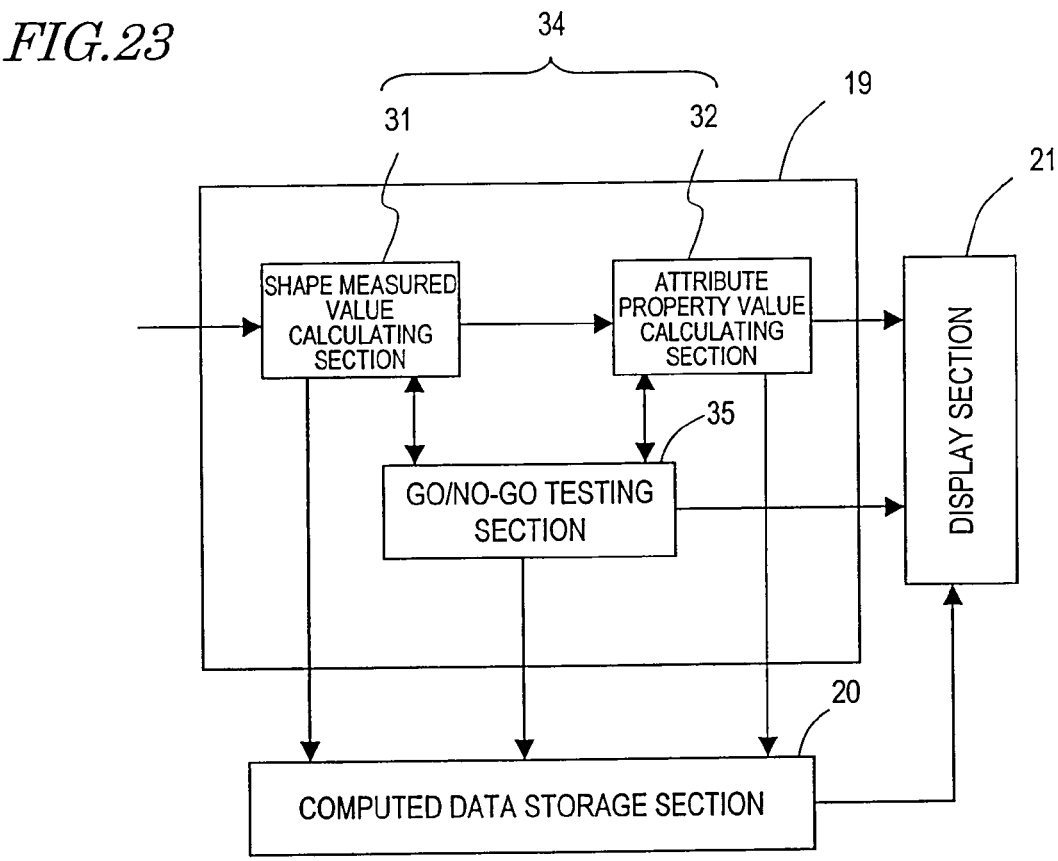

FIG. 23 is a block diagram showing a configuration for the core sections of an ultrasonic diagnostic apparatus according to a third preferred embodiment of the present invention.

Figure 24A:
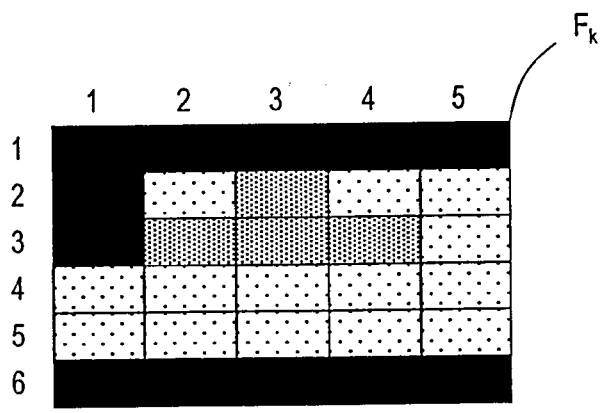

FIG. 24A schematically shows an image in which go/no-go information of elastic property is added to a spatial distribution image representing the elastic property.

Figure 24B:
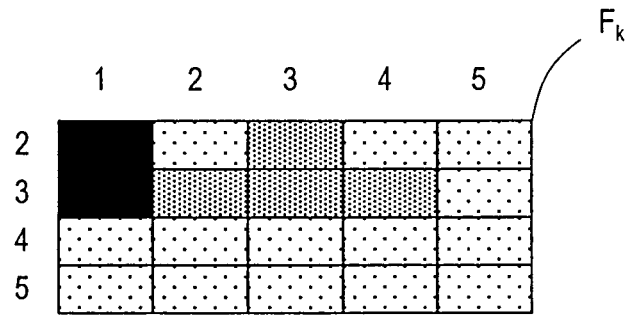

FIG. 24B schematically shows only a vascular wall portion extracted from the image shown in FIG. 24A.

Figure 25:
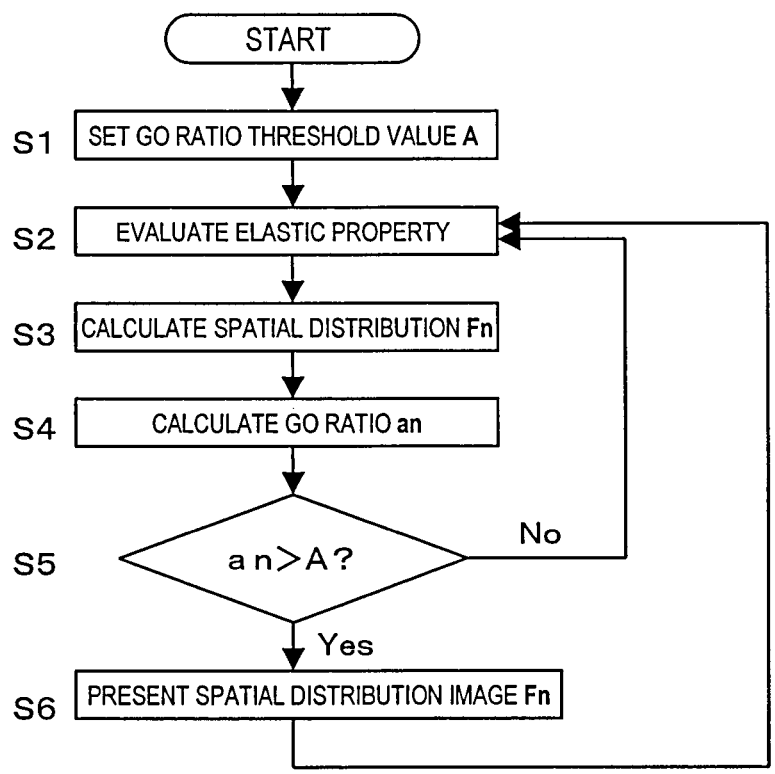

FIG. 25 is a flowchart showing an exemplary operation of an ultrasonic diagnostic apparatus according to the third preferred embodiment of the present invention.

Figure 26:
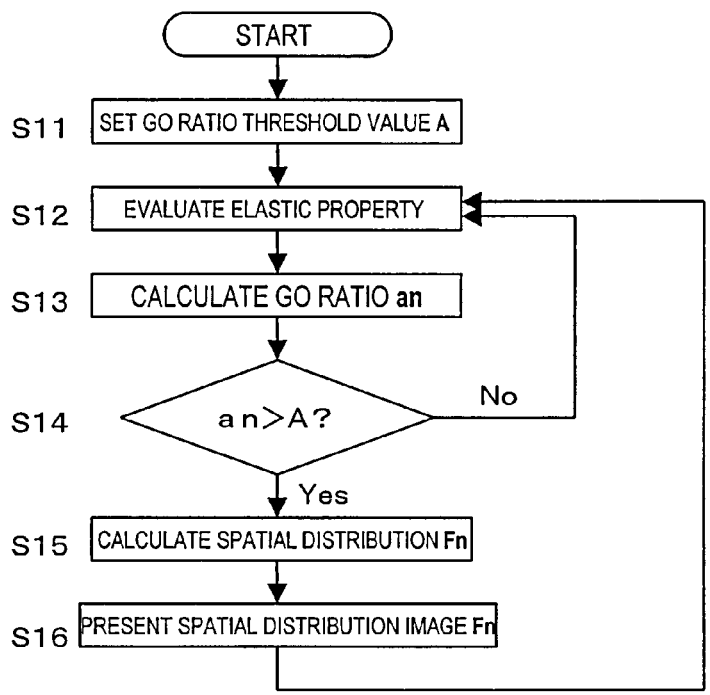

FIG. 26 is a flowchart showing another exemplary operation of the ultrasonic diagnostic apparatus of the third preferred embodiment of the present invention.

Figure 27:
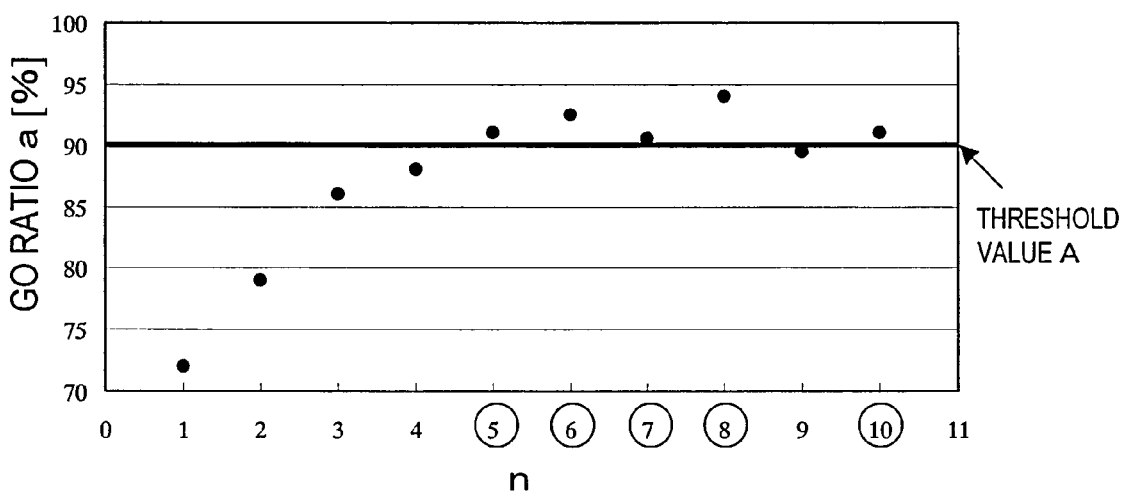

FIG. 27 is a graph schematically showing the go ratios to be calculated through the operation that follows the flowchart shown in FIG. 25 or 26.

Figure 28:
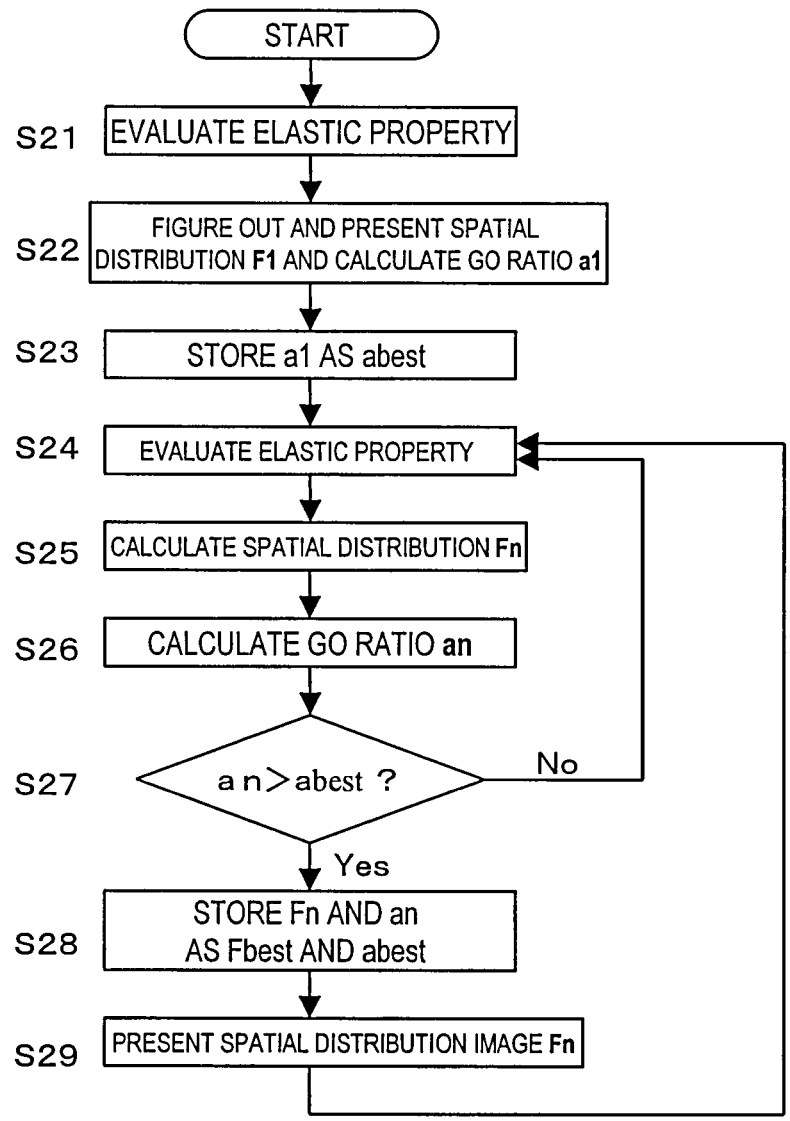

FIG. 28 is a flowchart showing still another exemplary operation of the ultrasonic diagnostic apparatus of the third preferred embodiment of the present invention.

Figure 29:
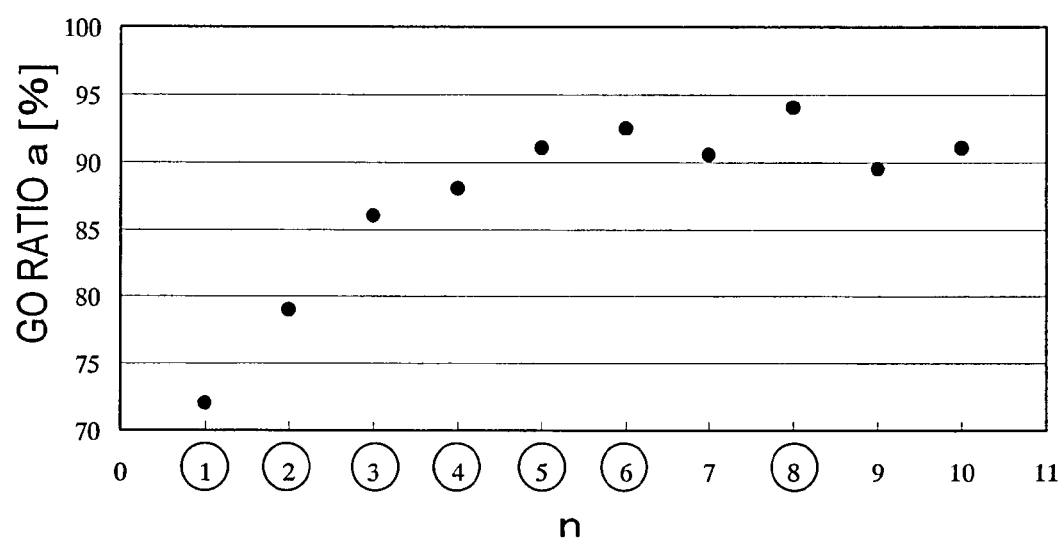

FIG. 29 is a graph schematically showing the go ratios to be calculated through the operation that follows the flowchart shown in FIG. 28.

DESCRIPTION OF REFERENCE NUMERALS 1 extravascular tissue
2 body surface
3 blood vessel
4 vascular anterior wall
5 blood
11 ultrasonic diagnostic apparatus
12 blood pressure manometer
13 ultrasonic probe
14 transmitting section
15 receiving section
16 time delay control section
17 phase detecting section
18 filter section
19 computing section
20 computed data storage section
21 display section
22 electrocardiograph
31 shape measured value calculating section
31a positional displacement calculating section
31b thickness variation calculating section
31c maximum/minimum value calculating section
32 attribute property value calculating section
33, 33' accuracy checking section
34 distribution image generating section
35 go/no-go testing section
40 vascular wall
41 ROI
60 organism
64 vascular wall
66 acoustic line
67 ultrasonic beam

BEST MODE FOR CARRYING OUT THE INVENTION

An ultrasonic diagnostic apparatus according to the present invention estimates the motion velocity of each portion of an object of measurement and also figures out the greatest thickness difference and elastic property of each very small area. The ultrasonic diagnostic apparatus of the present invention can be used effectively to evaluate the elastic property of each portion of an organism and also has sufficiently high spatial resolution. That is why the ultrasonic diagnostic apparatus of the present invention is preferably used to figure out the greatest thickness difference, strain and elastic property of a vascular wall.

Supposing $\Delta p$ is the difference between the maximum and minimum blood pressure values (i.e., pulse pressure), $\Delta h$ is the greatest thickness difference of the vascular wall during an arbitrary cardiac cycle, and H is the maximum thickness of the vascular wall, the strain is given by $\Delta h/H$ and the elastic property is given by $\Delta p \cdot H/\Delta h$. That is why to evaluate the strain and elastic property with good reliability, it is important to figure out the greatest thickness difference accurately. Thus, an ultrasonic diagnostic apparatus according to the present invention will be described as being applied to figuring out the greatest thickness difference of a vascular wall.

Figure 1:
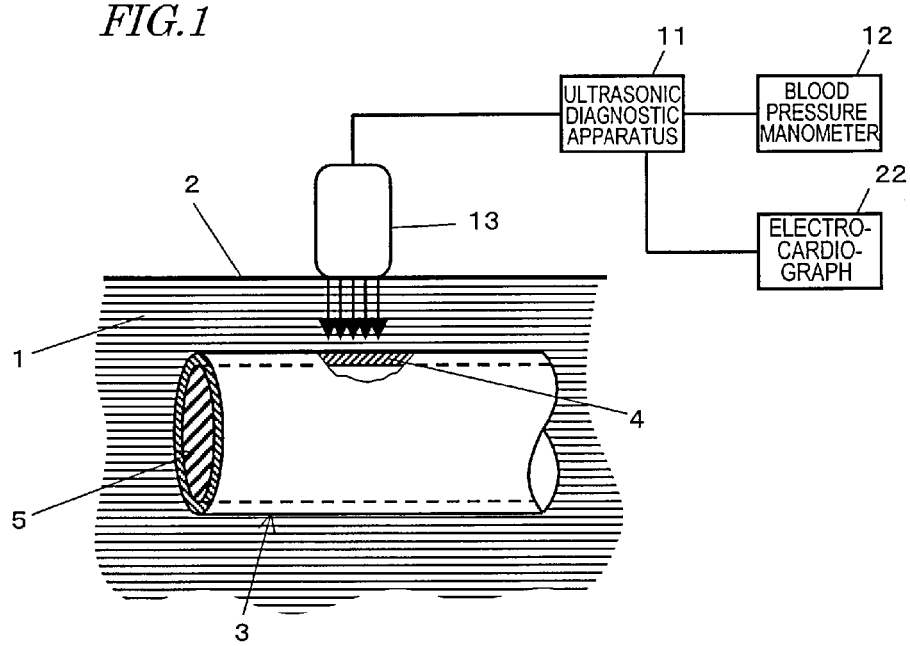
FIG. 1 is a block diagram showing an arrangement for a situation where an ultrasonic diagnostic apparatus according to the present invention is used to diagnose the tissue and attribute of a vascular wall.

FIG. 1 is a block diagram showing an arrangement for a situation where the ultrasonic diagnostic apparatus 11 of the present invention is used to diagnose the tissue and attribute of a vascular wall. This arrangement will be used in common in each of the preferred embodiments to be described below. An ultrasonic probe 13, connected to the ultrasonic diagnostic apparatus 11, is held in close contact with the body surface 2 of a person under test and transmits an ultrasonic wave into a body tissue including an extravascular tissue 1 and a blood vessel 3. The extravascular tissue 1 is made up of fats, muscles and so on. The transmitted ultrasonic wave is reflected by the blood vessel 3 and blood 5, scattered, and only a portion of it comes back to, and is received as an echo by, the ultrasonic probe 13. The ultrasonic probe 13 may be a known ultrasonic probe, which includes an array of ultrasonic vibrators (i.e., a group of ultrasonic vibrators) and which is used in a conventional ultrasonic diagnostic apparatus. The ultrasonic diagnostic apparatus 11 performs analysis and computations on the signal that has been received as an echo by the ultrasonic probe 13, thereby acquiring the mobility information of the extravascular tissue 1 and blood vessel 3. Also, a blood pressure manometer 12 is connected to the ultrasonic diagnostic apparatus 11 such that information about the blood pressure values of the person under measurement, collected by the blood pressure manometer 12, is input to the ultrasonic diagnostic apparatus 11.

In accordance with the method disclosed in Patent Document No. 1, the ultrasonic diagnostic apparatus 11 determines the instantaneous position of the object by a restricted minimum square method using both the amplitude and phase of a detection signal, thereby performing phase tracking highly accurately (where the magnitude of positional displacement has a measuring accuracy of about ±0.2 μm) and measuring variations in the position and thickness of a very small spot on the wall of the blood vessel 3 with time with sufficient precision. In addition, by using the blood pressure information obtained with the blood pressure manometer 12, the ultrasonic diagnostic apparatus 11 can also evaluate the elastic property of a very small spot on the wall of the blood vessel 3.

An electrocardiograph 22 is connected to the ultrasonic diagnostic apparatus 11, which receives an electrocardiogram from the electrocardiograph 22 and uses it as a trigger signal that determines the timings of measuring data acquisition and data resetting.

Embodiment 1

Figure 2:
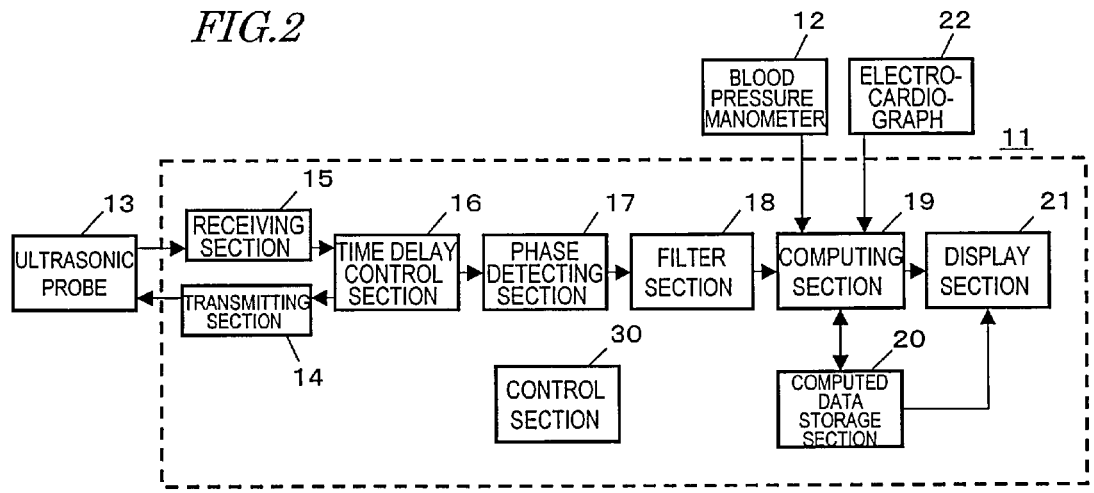
FIG. 2 is a block diagram showing a first preferred embodiment of an ultrasonic diagnostic apparatus according to the present invention.

Hereinafter, a first preferred embodiment of an ultrasonic diagnostic apparatus according to the present invention will be described. FIG. 2 is a block diagram showing a configuration for the ultrasonic diagnostic apparatus 11. The ultrasonic diagnostic apparatus 11 includes a transmitting section 14, a receiving section 15, a time delay control section 16, a phase detecting section 17, a filter section 18, a computing section 19, a computed data storage section 20, and a display section 21. The ultrasonic diagnostic apparatus 11 further includes a control section 30 (implemented as a microcomputer, for example) for performing an overall control on all of these sections.

The transmitting section 14 generates a predetermined drive pulse signal and outputs it to the ultrasonic probe 13. An ultrasonic transmitted wave, transmitted by the ultrasonic probe 13 in response to the drive pulse signal, is reflected and scattered by a body tissue such as the wall of the blood vessel 3 to produce an ultrasonic reflected wave, which is then detected by the ultrasonic probe 13. The frequency of the drive pulse that generates the ultrasonic wave is determined with the depth of the object of measurement and the velocity of the ultrasonic wave into consideration such that no ultrasonic pulses, adjacent to each other on the time axis, overlap with each other.

The receiving section 15 gets the ultrasonic reflected wave detected by the ultrasonic probe 13 and amplifies the detected signal, thereby generating a received signal. The receiving section 15 includes an A/D converting section for further converting the received signal into a digital signal. The transmitting section 14 and receiving section 15 may be made of electronic components, for example.

The time delay control section 16 is connected to the transmitting section 14 and receiving section 15 in order to control the time delay of the drive pulse signal to be supplied from the transmitting section 14 to a group of ultrasonic vibrators in the ultrasonic probe 13. In this manner, an ultrasonic beam of the ultrasonic transmitted wave to be transmitted from the ultrasonic probe 13 can have its acoustic line direction and depth of focus changed. Also, by controlling the time delay of the received signal that has been received by the ultrasonic probe 13 and then generated by the receiving section 15, the aperture size and depth of focus can be changed. The output of the time delay control section 16 is passed to the phase detecting section 17.

The phase detecting section 17 detects the phase of the received signal, of which the time delay has been controlled by the time delay control section 16, thereby splitting the signal into a real part signal and an imaginary part signal, which are then input to the filter section 18. The filter section 18 filters out RF components, the components that have not been reflected by the object of measurement and other noise components. The phase detecting section 17 and filter section 18 may be implemented as either a software program or hardware components. In this manner, phase detected signals, associated with respective points of measurement that are set in the tissue of the blood vessel 3 and each including a real part signal and an imaginary part signal, are generated.

Figure 3:
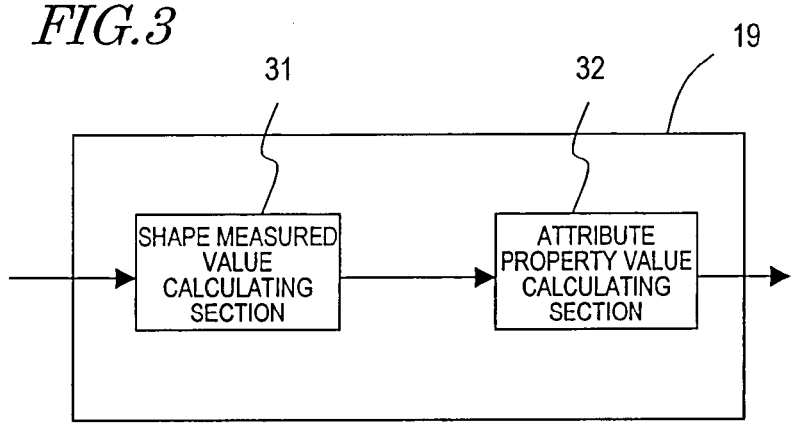
FIG. 3 is a block diagram showing the configuration of the computing section of the ultrasonic diagnostic apparatus shown in FIG. 2.

As shown in FIG. 3, the computing section 19 includes a shape measured value calculating section 31 and an attribute property value calculating section 32. The electrocardiogram obtained by the electrocardiograph 22 is input to the computing section 19 and used as a trigger signal for determining the timings of measuring data acquisition and data resetting. For this purpose, the electrocardiograph 22 may be replaced with any other biomedical signal detecting means such as a phonocardiograph or a sphygmograph. In that case, a phonocardiogram or a sphygmogram may be used as a trigger signal instead of the electrocardiogram.

The shape measured value calculating section 31 calculates the magnitude of positional displacement (i.e., positional displacement with time) between multiple measuring points, which are set inside the tissue of the blood vessel 3, based on the real part signal and imaginary part signal of the phase detected signal. The magnitude of positional displacement can also be figured out by calculating the motion velocity of a measuring point (i.e., a tracking point) and by integrating this motion velocity. Then, by calculating the difference between two magnitudes of positional displacements, which have been figured out at two arbitrarily selected points, among those magnitudes of positional displacements, the variation in thickness between the two points can be calculated. If either the initial values of the two points or the initial value of the difference between the magnitudes of positional displacements at the two points is given, then the thickness between the two points can be calculated.

It should be noted that the two points that define either the thickness or the variation in thickness do not have to agree with the measuring points that have been set inside the tissue of the blood vessel 3. Instead, the central one of the measuring points may be used. In that case, the magnitudes of positional displacements at the measuring points, of which the central one has been defined, is preferably averaged and the resultant averaged magnitude of positional displacement is preferably used. If multiple measuring points are used, the representative one of the measuring points and the magnitude of positional displacement at that point may be either simply calculated or weighted. In any case, the two points and the magnitudes of positional displacements at those points just need to be obtained with respect to multiple measuring points.

The attribute property value calculating section 32 calculates the greatest thickness difference based on the difference between the maximum and minimum values of the thickness variations calculated, and evaluates the elastic property of the tissue between the two points based on the blood pressure data supplied from the blood pressure manometer 12. Alternatively, the elastic property may also be evaluated at one point between two arbitrary points. However, the ultrasonic probe for used in this preferred embodiment has an array of ultrasonic vibrators, and therefore, can evaluate the elastic property at every point within an arbitrary area of the given cross-sectional plane.

The display section 21 maps the greatest thickness difference, strain or elastic property that has been obtained in this manner from the vital tissue, thereby presenting a spatial distribution image, representing the spatial distribution of the shape measured values or attribute property values, every cardiac cycle. The spatial distribution image may be one-dimensional, two-dimensional or even three-dimensional. If the image is presented in a color or a tone associated with the shape measured value or attribute property value, the results of measurements can be understood more easily.

Figure 4A:
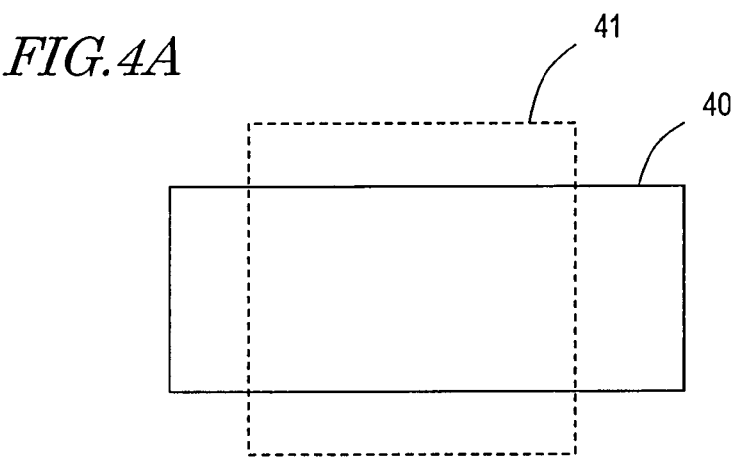
FIG. 4A schematically illustrates an ROI that is defined on a vascular wall image presented on a display section.
Figure 4B:
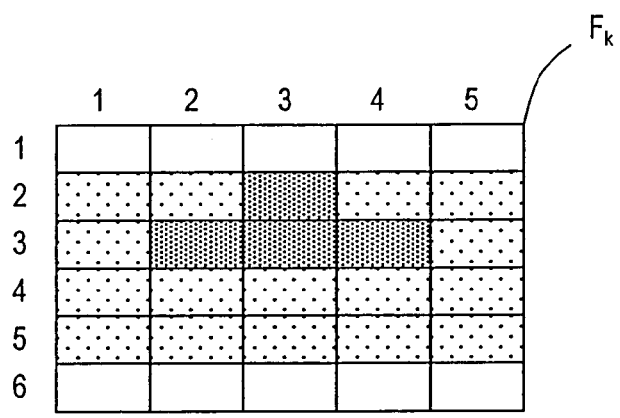
FIG. 4B schematically illustrates a two-dimensional elastic property image presented on the display section.

In this case, the operator can define an arbitrary area, in which the shape measured values or attribute property values should be obtained, by specifying an ROI (=region of interest) on the display section 21. The ROI is shown to allow the operator to define the area in which the measured values should be obtained. And the size and position of the ROI can be freely set by way of the interface section (not shown) of the ultrasonic diagnostic apparatus 11 while being checked on the display section 21. FIG. 4A schematically illustrates the vascular wall 40 and ROI 41 that are presented on the display section 21. The area defined by the ROI 41 includes a tissue other than the vascular wall 40. The image of the vascular wall 40 can be generated by modulating the received signal with a luminance associated with the amplitude or intensity differently from the calculations described above. FIG. 4B shows the elastic property of the vascular wall 40 in the area defined by the ROI 41. In the area defined by the ROI 41, image data items $f(k)_{11}$ through $f(k)_{65}$, which have been mapped to make a matrix of six rows and five columns, are arranged, thereby forming a spatial distribution image Fk. As described above, the image data items $f(k)_{11}$ through $f(k)_{65}$ represent the shape measured value (e.g., the greatest thickness difference) or the attribute property value (e.g., strain or elastic property) of a vital tissue.

Data about the magnitudes of positional displacement, variations in thickness, and elastic property that have been figured out by the computing section 19 may be stored in, and readily read out from, the computed data storage section 20, and may also be input to the display section 21 so as to be visualized into a two-dimensional image. Furthermore, if the display section 21 is connected to the computed data storage section 20, those various data stored may also be presented on the display section 21 when required. Those data computed by the computing section 19 are preferably output to both the display section 21 and the storage section 20 so as to be presented in real time and saved for future use at the same time. However, those data may be output to just one of the display section 21 and the storage section 20.

Figure 5:
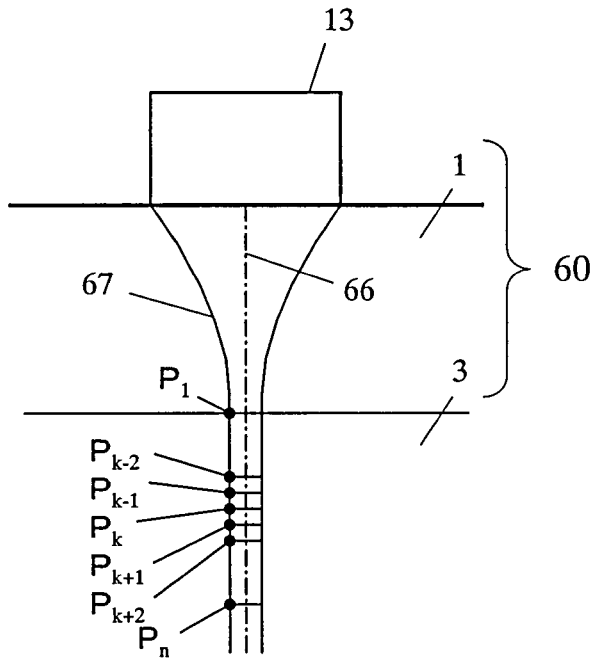
FIG. 5 schematically illustrates an ultrasonic beam propagating through a tissue of an organism.

Next, it will be described in detail with reference to FIGS. 5, 6 and 7 how to calculate the magnitude of positional displacement of a body tissue. As shown in FIG. 5, an ultrasonic transmitted wave, emitted from the ultrasonic probe 13, propagates as an ultrasonic beam 67 with a certain finite width through the extravascular tissue 1 and blood vessel 3 of the organism 60. In the meantime, a portion of the ultrasonic wave is either reflected or scattered by the extravascular tissue 1 or the blood vessel 3 back toward the ultrasonic probe 13 and received there as an ultrasonic reflected wave. The ultrasonic reflected wave is detected as a time series signal r(t). The closer to the ultrasonic probe 13 a portion of the tissue that has reflected the ultrasonic wave to produce the time series signal, the closer to the origin the signal is located on the time axis. The width (i.e., beam spot size) of the ultrasonic beam 67 can be controlled by changing the time delay.

As described above, the ultrasonic reflected wave may be produced by the extravascular tissue 1, blood vessel 3 and blood 5. However, since the vascular wall tissue is the object of measurement in this preferred embodiment, the following description will be focused on only the blood vessel 3 (in particular, the vascular anterior wall that is closer to the body surface). A plurality of measuring points $P_n$, which are located on an acoustic line 66 (i.e., the center axis of the ultrasonic beam) on the vascular anterior wall, are arranged at regular intervals in the order of $P_1, P_2, P_3, \ldots, P_k, \ldots$ and $P_n$ (where n is natural number that is equal to or greater than three) where $P_1$ is a located closest to the ultrasonic probe 13. Supposing coordinates are defined in the depth direction such that the upper half of FIG. 5 is positive domain and the lower half thereof is negative domain and the coordinates of the measuring points $P_1, P_2, P_3, \ldots, P_k, \ldots$ and $P_n$ are represented by $Z_1, Z_2, Z_3, \ldots, Z_k, \ldots$ and $Z_n$, an ultrasonic wave reflected from a measuring point $P_k$ is located at $t_k = 2Z_k/c$ on the time axis, where c is the velocity of the ultrasonic wave in the body tissue. The reflected wave signal r(t) has its phase detected by the phase detecting section 17 and the phase-detected signal is split into a real part signal and an imaginary part signal, which are then passed through the filter section 18.

As described above, the ultrasonic diagnostic apparatus 11 sequentially calculates the magnitude of positional displacement, the variation in thickness, and the maximum and minimum values of the thickness variations based on the phase-detected signal. As shown in FIG. 7, the computing section 19 includes a positional displacement calculating section 31a, a thickness variation calculating section 31b and a maximum/minimum value calculating section 31c to obtain these shape measured values. Under the restriction that the amplitude does not change, but only the phase and reflection spot change, between the reflected wave signal r(t) and another reflected wave signal r(t+Δt) obtained after a very small amount of time Δt, the positional displacement calculating section 31a calculates the phase difference by a minimum square method so as to minimize the waveform mismatch between the reflected wave signals r(t) and r(t+Δt). That is to say, the positional displacement calculating section 31a adopts a restricted minimum square method. The motion velocity $V_n(t)$ of the measuring point $P_n$ is derived from this phase difference and then integrated, thereby obtaining the magnitude of positional displacement $d_n(t)$.

Figure 6:
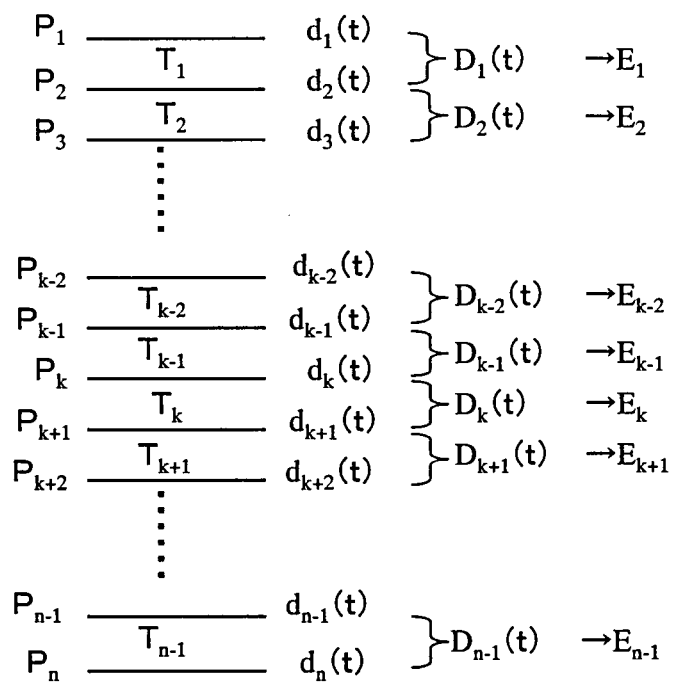
FIG. 6 shows the relationship between the measuring point and the elasticity at the measuring point.
Figure 7:
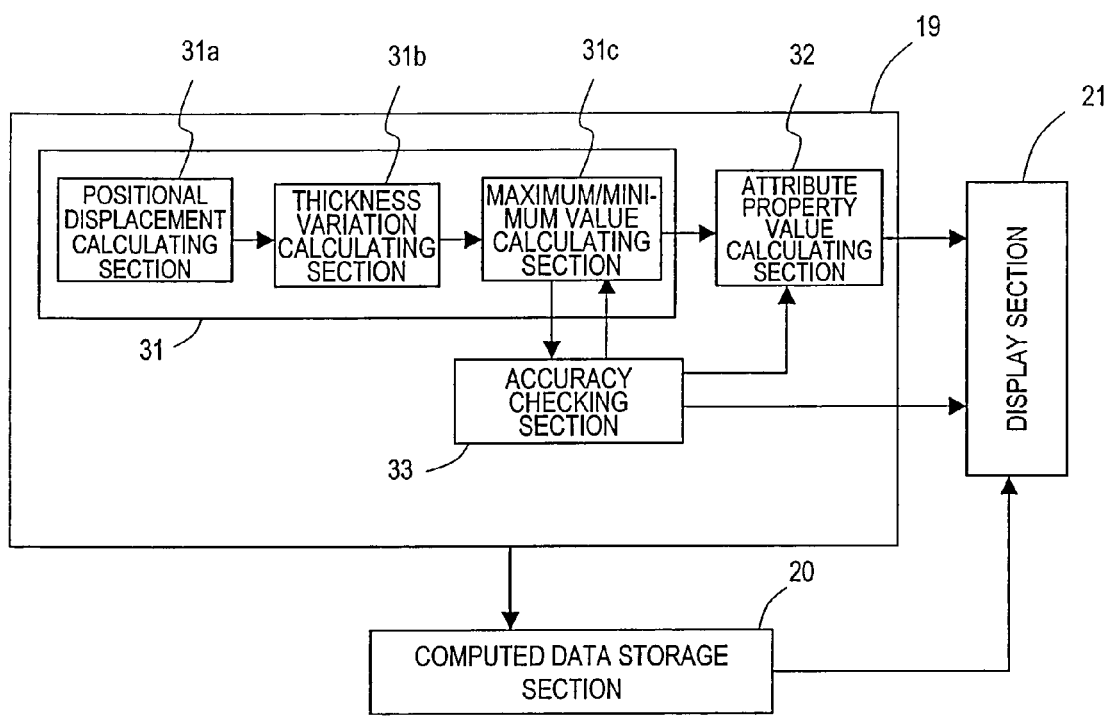
FIG. 7 is a block diagram showing the detailed configuration of core sections of the ultrasonic diagnostic apparatus shown in FIG. 2.

FIG. 6 shows the relationship between the measuring point $P_n$, and the tissue under test $T_n$, of which the elasticity needs to be calculated. A tissue under test $T_k$ is located between two adjacent measuring points $P_k$ and $P_{k+1}$ so as to have a thickness h. In this preferred embodiment, a number (n−1) of tissues under test $T_1$ through $T_{n-1}$ can be sampled from a number n of measuring points $P_1$ through $P_n$.

The thickness variation calculating section 31b calculates the variation $D_k(t)$ in thickness as the difference between the magnitudes of positional displacement $d_k(t)$ and $d_{k+1}(t)$ of the measuring points $P_k$ and $P_{k+1}$ (i.e., $D_k(t)=d_k(t)-d_{k+1}(t)$).

Furthermore, the maximum/minimum value calculating section 31c obtains the maximum and minimum values of the thickness variations. The thickness of the tissue $T_k$ of the vascular anterior wall varies when the blood flowing through the blood vessel, made up of the vascular anterior wall, changes with the cardiac rate. Accordingly, the elasticity $E_k$ (i.e., the strain rate) of the tissue under test $T_k$ in the vascular radial direction is given by:

$$E_k = (\Delta p \times H_k)/\Delta h_k$$

where $H_k$ is the maximum thickness of the tissue under test $T_k$ (i.e., the value associated with the lowest blood pressure), $\Delta h_k$ is the difference between the maximum and minimum thickness variations $D_k(t)$ of the tissue under test, and $\Delta p$ is pulse pressure that is the difference between the lowest and highest blood pressures.

In the example described above, the elasticity of the tissue under test $T_n$ is calculated between two adjacent measuring points. However, the elasticity may also be calculated between two arbitrary ones of the multiple measuring points. In that case, the elasticity can be calculated in a similar manner by using the maximum thickness between the two points selected and the maximum and minimum thickness variations between the two points selected.

If the tissue under measurement is a circulatory organ such as a vascular wall, then the greatest thickness difference $\Delta h$ and pulse pressure $\Delta p$ are both updated every cardiac cycle. That is why the elastic property is preferably evaluated in sync with every cardiac cycle. To calculate the greatest thickness difference $\Delta h$ in one cardiac cycle, the maximum and minimum thickness variations in one cardiac cycle need to be obtained. According to the present invention, these maximum and minimum thickness variations are searched for in a period that is shorter than one cardiac cycle. Hereinafter, the timings of measuring these numerical values will be described in detail.

Graphs 8a, 8b and 8c of FIG. 8 respectively show the magnitude of positional displacement, variation in thickness, and variation in the inside diameter of the blood vessel as measured by the ultrasonic diagnostic apparatus 11 at an arbitrary point on the vascular wall of a human carotid artery. On the other hand, graphs 8d, 8e and 8f of FIG. 8 respectively show the electrocardiogram, phonocardiogram and pulse wave, which are biomedical signals obtained by measuring the displacements shown in graphs 8a, 8b and 8c of FIG. 8. In all of these graphs 8a through 8f of FIG. 8, the abscissa represents the time. That is to say, these graphs share the same time axis in common. Meanwhile, the chart 8g of FIG. 8 shows the cardiac cycle phenomena on the time axis of portions 8a through 8f.

As shown in the chart 8g of FIG. 8, one cardiac cycle is roughly divided into a systolic phase and a diastolic phase. The systolic phase is subdivided into a preejection period and an ejection period and the diastolic phase is subdivided into an isovolumetric relaxation period, a diastolic filling period and an atrial systolic period. The systolic phase substantially corresponds to a range that starts with the beginning of Q wave and terminates with the end of T wave on the electrocardiogram (i.e., graph 8d) and to a range that starts with the beginning of I sound and terminates with the end of II sound on the phonocardiogram (i.e., graph 8e). On the other hand, the diastolic phase substantially corresponds to a range that starts with the end of T wave and terminates with the beginning of Q wave on the electrocardiogram and to a range that starts with the beginning of II sound and terminates with the beginning of I sound on the phonocardiogram. In FIG. 8, one cardiac cycle, which is triggered by the beginning of a systolic phase as observed in a heart, is indicated by the dashed lines.

The magnitude of positional displacement, variation in thickness and variation in the inside diameter of the blood vessel shown in graphs 8a, 8b and 8c and the pulse wave shown in graph 8f are measured at the carotid artery, which is located away from the heart. That is why when about 0.1 second has passed after various events of one cardiac cycle have occurred in the heart, phenomena corresponding to these events of the heart are observed on these magnitudes of displacement and a pulse wave. For example, the systolic phase of the pulse wave (see graph 8f) starts with S wave but its timing trails by about 0.1 second behind the beginning of the systolic phase as indicated by the dashed line. In FIG. 8, one cardiac cycle, which is triggered by the beginning of a systolic phase as observed in the carotid artery, is indicated by the one dot chain.

When blood is ejected from the heart, the pulse wave curve rises steeply from S wave into P wave. After having reached the peak of the P wave, the pulse wave curve makes a small upward hump of T wave, makes a notch of C wave, makes another small upward hump of D wave, and then falls gently. The C and D waves are called "dichrotic notch" and "dichrotic wave", respectively, and are events brought about by the closure of the aortic valve. In the variation in the thickness of the carotid artery shown in graph 8b, the maximum value b1 is encountered at the same time as the S wave of the pulse wave, while the minimum value b2 is found at the same time as the P wave of the pulse wave. That is to say, it can be seen that the greatest thickness difference $\Delta h$ does not have to be calculated in the overall cardiac cycle but in just a period in which the S and P waves of the pulse waves are monitored. More specifically, it can be seen that the period in which the maximum value b1 should be found has only to fall within a time period including at least the S wave of the pulse wave and that the period in which the minimum value b2 should be found has only to fall within a time period including at least the P wave of the pulse wave. Likewise, the maximum and minimum blood pressures for calculating the pulse pressure $\Delta p$ can also be obtained from the time periods including these S and P waves. Furthermore, the maximum thickness H can be obtained when the thickness variation reaches its maximum value b1.

Consequently, the elastic property of a circulatory organ such as the vascular wall of an organism can be measured in either a period including the ejection period and the ventricular systolic period (during which the S and P waves of the pulse wave are observed) in one cardiac cycle or a period including at least a part of the ejection period and at least a part of the ventricular systolic period. Stated otherwise, no maximum or minimum thickness variation is present within the diastolic phase of one cardiac cycle. Accordingly, even if measurements were done in this phase to search for the maximum and minimum values, no desired maximum and minimum values should be obtained. That is why the magnitude of positional displacement does not have to be measured continuously all through one cardiac cycle but has only to be measured at least until a period including the P wave of the pulse wave if the measurement is triggered with the S wave of the electrocardiogram and the I sound of the phonocardiogram.

According to the present invention, by taking advantage of such a tendency of the thickness variation, the periods for finding the maximum and minimum thickness variations within one cardiac cycle are set shorter than one cardiac cycle. More specifically, a maximum value finding period for finding the maximum value of the thickness variations and a minimum value finding period for finding the minimum value thereof are provided as respective partial periods of one cardiac cycle. The maximum value finding period preferably includes at least a time when the S wave of the pulse wave produces and the minimum value finding period preferably includes at least a time when the P wave of the pulse wave produces. These periods are preferably as short as possible. And the maximum value finding period and the minimum value finding period preferably do not overlap with each other. The maximum/minimum value calculating section 31c of the shape measured value calculating section 31 finds the maximum thickness variation during the maximum value finding period defined and the minimum thickness variation during the minimum value finding period defined, respectively.

FIG. 9 shows an example in which a maximum value finding period and a minimum value finding period are defined within one cardiac cycle. In FIG. 9, the period between the two dashed lines represents one cardiac cycle. By shortening the maximum value and minimum value finding periods, noise is less likely recognized as a maximum or minimum value by mistake. For example, if each of the maximum value and minimum value finding periods is defined so as to have a duration corresponding to approximately 10% of one cardiac cycle, then the chances of noise interference can be reduced to about one-fifth. In addition, by shortening the measuring periods, the complexity of computations to be done on the measured values can also be cut down. As a result, the manufacturing costs of the ultrasonic diagnostic apparatus can be reduced since there is no need to introduce a lot of memories into the ultrasonic diagnostic apparatus or use a high-performance computer with high computational processing ability. Or an ultrasonic diagnostic apparatus that can get measuring done at high speeds is realized.

A number of measuring sample points are preferably set within the maximum value finding period and/or the minimum value finding period. Just one sample point may be set within the maximum value or minimum value finding period to cut down the influence of noise. Strictly speaking, however, one cardiac cycle is variable with a respiratory cycle, for example, and therefore, does not have a constant length. That is why to find the maximum and minimum values, a number of sample points are preferably set for each of the maximum and minimum value finding periods. When a number of sample points are set, the average of multiple values may be calculated within the maximum value (or minimum value) finding period and used as the maximum value (or minimum value) of the thickness variations.

As is clear FIG. 8, the times when the S and P waves of the pulse wave are monitored and the times when the maximum and minimum thickness variations b1 and b2 are obtained can be set easily by using the biomedical signal. For example, when the electrocardiograph 22 is used as biomedical signal detecting means, the maximum value finding period may be set as a period that lasts 0.1 second since the R wave was detected and the minimum value finding period may be set as a period that begins 0.2 second after the R wave was detected and ends 0.3 second after the R wave was detected. Then, the maximum and minimum thickness variations can be obtained effectively. Optionally, the R wave may be replaced with P wave, Q wave, S wave, T wave or U wave, or the maximum value finding period may be defined as lasting an amount of time corresponding to 10% of one cardiac cycle since the S wave. Even so, similar effects are also achieved.

Alternatively, if a phonocardiograph is used as biomedical signal detecting means, the maximum value finding period may be set as a period that lasts 0.1 second since the I sound was detected and the minimum value finding period may be set as a period that begins 0.2 second after the I sound was detected and ends 0.3 second after the I sound was detected. Then, the maximum and minimum thickness variations can also be obtained effectively. Optionally, the I sound may be replaced with II sound, III sound or IV sound. Alternatively, the maximum value finding period may be defined as lasting an amount of time corresponding to 10% of one cardiac cycle since the I sound was detected. Even so, similar effects are also achieved.

As another alternative, if a pulse monitor is used as biomedical signal detecting means, the maximum value finding period may be set as a period that begins 0.05 second before the S wave is detected and ends 0.05 second after the S wave was detected, while the minimum value finding period may be set as a period that begins 0.05 second before the P wave is detected and ends 0.05 second after the P wave was detected. Then, the maximum and minimum thickness variations can also be obtained effectively. Optionally, the S and P waves may be replaced with T wave, C wave or D wave. Alternatively, the maximum value finding period may be defined as beginning earlier than the detection of S wave by an amount of time corresponding to 5% of one cardiac cycle and ending later than the detection of S wave by the amount of time corresponding to 5% of one cardiac cycle. Even so, similar effects are also achieved.

Furthermore, instead of providing a separate instrument for detecting the biomedical signal outside of the ultrasonic diagnostic apparatus 11 and inputting the biomedical signal, the numerical values got by the ultrasonic diagnostic apparatus 11 may also be used as a trigger signal. As shown in graph 8a of FIG. 8, there are local maximum and minimum points such as the points a1, a2 and a3, where the magnitude of positional displacement changes uniquely, in the curve representing the magnitudes of positional displacement at arbitrary points on the carotid artery under measurement. That is why even if those points a1, a2 and a3 are extracted by the computing section 19, the maximum and minimum thickness variation finding periods can also be defined. It should be noted that the point a1 is an event resulting from a point with the lowest blood pressure at the measuring point on the blood vessel 3, the point a2 is an event resulting from a point with the highest blood pressure at the measuring point on the blood vessel 3, and the point a3 is an event resulting from a dichrotic notch.

If the measuring period is defined based on the magnitudes of positional displacements, the maximum and minimum thickness variations can be easily obtained by defining the maximum value finding period as a period that begins 0.5 second before the point a1 and ends 0.05 second after the point a1 and the minimum value finding period as a period that begins 0.5 second before the point a2 and ends 0.05 second after the point a2, respectively. Alternatively, the point a3 may also be used as a reference point. As another alternative, the maximum value finding period may also be defined as a period that begins earlier than the point a1 by an amount of time corresponding to 5% of one cardiac cycle and ends later than the point a1 by the same amount of time.

Optionally, as shown in graph 8c, the points c1, c2 and c3 may be extracted from the curve representing the variation in the inside diameter of the blood vessel and used for defining the measuring period. Or the points b1, b2 and b3 may be extracted from the curve representing the thickness variation shown in graph 8b and used for setting the measuring period.

To define the maximum and minimum thickness variation finding periods by using the biomedical signal generated by the biomedical signal detecting means, the electrocardiogram obtained by the electrocardiograph 22 may be input to the computing section 19 as shown in FIGS. 1 and 2. If the R wave is detected in the electrocardiogram, the magnitude of positional displacement and the thickness variation may start to be calculated. A period lasting 0.1 second since the R wave was detected is defined as a maximum value finding period and the maximum thickness variation is found during this period.

Next, a period that begins 0.2 second after the R wave was detected and ends 0.3 second after the R wave was detected is defined as the minimum value finding period, and the minimum thickness variation is found during this period. When 0.3 second has passed since the R wave was detected, the calculation of the magnitude of positional displacement and thickness variation may be stopped.

The R wave may be detected by making the computing section 19 use the amplitude of the electrocardiogram, values obtained by differentiating the electrocardiogram, and their timings of appearance. Alternatively, the electrocardiograph 22 may also detect the R wave and may output a control signal to the computing section 19 on detecting the R wave.

Also, in the T or U wave obtained from the electrocardiograph 22, for example, the timing of a specific signal that is used as a reference for setting the maximum value or minimum value find period may be close to, or be posterior to, the time when the maximum or minimum value of the thickness variations is detected. In that case, the specific signal may be used as a trigger for setting the measuring period in the next cardiac cycle that follows the period in which the specific signal used as a trigger is detected. Also, the computations for finding the maximum and minimum values of the thickness variations may be carried out either in real time during the period defined by the specific signal, for example, or not during that period.

Considering the individual differences among persons under test, each of the maximum and minimum value finding periods preferably has a length corresponding to 1% through 25% of one cardiac cycle. The reasons are as follows. Specifically, if the measuring period were shorter than 1% of one cardiac cycle, then at least one of the maximum and minimum thickness variations could not be obtained. However, if the measuring period were longer than 25% of one cardiac cycle, then the effects to be achieved by shortening the measuring period could not be achieved fully and the measurement could be subject to noise more easily. For these reasons, the measuring period, defined by using the biomedical signal as a trigger, preferably falls within this range. By setting the measuring period within this range, the computational complexity and the influence of noise would be reduced by approximately 50% to 99%.

Also, while diagnosed by the ultrasonic diagnostic apparatus, the organism is laid to rest and is likely to have little variation in cardiac cycle. That is why the maximum and minimum value finding periods do not have to be defined every cardiac cycle. Alternatively, once defined in accordance with the biomedical information described above, the measuring period may be repeated at the same intervals a number of times. Meanwhile, if the biomedical signal is detected every cardiac cycle and if the measuring period is defined based on that biomedical signal, then the elastic property can be evaluated just as intended even when the organism has an irregular cardiac cycle due to arrhythmia, for example.

In the preferred embodiment described above, the measuring period is supposed to be set with the specific signal obtained by only one type of biomedical signal detecting means. Optionally, the measuring period may also be defined by specific signals obtained by a plurality of biomedical signal detecting means. For example, the R wave of the electrocardiogram may be used as a signal that defines the maximum value finding period and the point c3 of the variation in the inside diameter of the blood vessel may be used as a signal that defines the minimum value finding period.

Also, in the preferred embodiment described above, the greatest thickness difference is obtained by finding the maximum and minimum thickness variations. Alternatively, the thicknesses themselves may be measured and the greatest thickness difference may be obtained from the maximum and minimum thicknesses. Suppose the thickness variation is already known. In that case, if the thickness when the thickness variation starts to be measured is known, then the variation in thickness with time can be obtained as the sum of the thickness at the start of measuring and the thickness variation. The thickness at the start of measuring is nothing but the initial value of the distance between two arbitrary points to calculate the magnitudes of positional displacement for, and is a known parameter for the ultrasonic diagnostic apparatus 11 of this preferred embodiment.

By finding the maximum and minimum values of the thickness variations by the method described above, the influence of noise can be reduced. However, the maximum or minimum value of the thickness variations within one cardiac cycle may sometimes be located outside of the maximum value or minimum value finding period. The reasons are as follows.

FIGS. 10A and 10B schematically show measuring points $P_1$ through $P_7$ on an acoustic line of an ultrasonic wave that has been transmitted toward the blood vessel 3. In FIG. 10A, the points $P_1$ and $P_2$ are set in the vascular anterior wall 4, the points $P_3$, $P_4$ and $P_5$ in the blood 5, and the points $P_6$ and $P_7$ in the vascular posterior wall 6.

FIG. 11A shows how the positional displacement waveforms $d_1(t)$ through $d_7(t)$ at the respective measuring points $P_1$ through $P_7$ change in one cardiac cycle. The points $P_1$ and $P_2$ in the vascular anterior wall 4 shift upward (i.e., toward the ultrasonic probe 13) as the blood vessel dilates and shift downward as the blood vessel is constricted. On the other hand, the points $P_6$ and $P_7$ in the vascular posterior wall 6 shift downward as the blood vessel dilates and shift upward as the blood vessel is constricted. The more distant from the center of the blood vessel the given point is, the smaller the amplitude of positional displacement in the wall of the blood vessel 3. That is to say, the amplitude of $d_1(t)$ is smaller than that of $d_2(t)$ in the vascular anterior wall 4 and the amplitude of $d_7(t)$ is smaller than that of $d_6(t)$ in the vascular posterior wall 6.

If these positional displacement waveforms $d_1(t)$ through $d_7(t)$ are obtained at the measuring points $P_1$ through $P_7$, the waveforms $D_1$ through $D_6$ showing the variations in thickness between two adjacent measuring points are given by $D_n(t)=d_n(t)-d_{n+1}(t)$ as shown in FIG. 11B.

As shown in FIG. 11B, the thickness variation waveforms $D_1(t)$ and $D_6(t)$ protrude downward and their shapes are similar to that of the graph 8b shown in FIG. 8. In the thickness variation waveforms $D_1(t)$ and $D_6(t)$, the maximum value thereof precedes the minimum value thereof within one cardiac cycle.

Meanwhile, the thickness variation waveform $D_2(t)$ including the boundary between the vascular anterior wall 4 and the blood 5 and the thickness variation waveform $D_5(t)$ including the boundary between the blood 5 and the vascular posterior wall 6 protrude upward. Also, the blood 5 scatters the ultrasonic waves to a much lesser degree than the tissue and does not show variations synchronously with the palmus unlike the tissue, and therefore, includes a lot of noise components. That is why the thickness variation waveforms $D_3(t)$ and $D_4(t)$ in the blood 5 are either random waveforms with a lot of noise components or waveforms showing almost no variations.

Also, depending on the measuring point, the ultrasonic reflected wave may have an extremely small amplitude for some reason or include some noise. In that case, the magnitude of positional displacement calculated by using a signal representing the wave that has been reflected from such a point may have an inaccurate value. Specifically, its waveform may have an excessively large waveform or an excessively small waveform overall. In such a situation, the thickness variation waveforms obtained based on those magnitudes of positional displacements will be graphs with inverted positive and negative values just like the waveforms $D_2(t)$ and $D_5(t)$ mentioned above.

When such thickness variation waveforms with inverted positive and negative values are obtained, correct maximum and minimum values cannot be obtained even by finding the maximum value within the maximum value finding period and the minimum value within the minimum value finding period, respectively. As a result, the greatest thickness difference, strain and elastic property, calculated based on the maximum and minimum values thus obtained, cannot be correct values, either, and those values should have low reliability. To make the operator of this ultrasonic diagnostic apparatus or a doctor correctly recognize these results of measurements as measuring data with low reliability, the ultrasonic diagnostic apparatus 11 of this preferred embodiment further includes an accuracy checking section 33 for checking the accuracy of the greatest thickness difference, the strain and the elastic property (see FIG. 7).

The accuracy checking section 33 compares the maximum value of the thickness variation waveform during the maximum value finding period with the minimum value thereof during the minimum value finding period, thereby checking the accuracies of the greatest thickness difference, strain and elastic property based on the results of the comparison. Specifically, if the maximum value found during the maximum value finding period is $D_{max}$ and the minimum value found during the minimum value finding period is $D_{min}$, the accuracy checking section 33 determines whether or not the maximum and minimum values satisfy the following Inequality (1):

$$D_{max} > D_{min} \tag{1}$$

If the maximum and minimum values satisfy this Inequality (1), then the accuracy checking section 33 determines that the maximum and minimum values that have been found from the thickness variation waveform are correct values and that the greatest thickness difference, strain and elastic property, calculated based on these values, have high accuracies. This is because in the correct thickness variation $D_k(t)$, the maximum and minimum values of the thickness variation waveform during one cardiac cycle are included in the maximum value finding period and the minimum value finding period, respectively. If the thickness variation waveform shown in FIG. 9 has been obtained, then D(t1))>D(t2) and Inequality (1) is satisfied. Consequently, the greatest thickness difference, strain and elastic property to be calculated based on the maximum value D(t1) and the minimum value D(t2) have high accuracies.

On the other hand, if the thickness variation waveform has inverted positive and negative values as shown in FIG. 12, then the maximum value D'(t1') found during the maximum value finding period is smaller than the minimum value D'(t2') found during the minimum value finding period (i.e., D'(t1')<D'(t2')) and fail to satisfy Inequality (1). Consequently, the greatest thickness difference, strain and elastic property to be calculated based on the maximum value D'(t1') and the minimum value D'(t2') have low accuracies.

When determining, based on the maximum and minimum values, that the greatest thickness difference, strain or elastic property has a low accuracy, the accuracy checking section 33 sets the greatest thickness difference, strain or elastic property to a predetermined value (e.g., zero or a negative value). Alternatively, the accuracy checking section 33 may generate information showing the degree of accuracy. The information showing the degree of accuracy is either "high accuracy" or "low accuracy". And the accuracy checking section 33 may generate an appropriate numerical value (consisting of zeros and ones, for example) in accordance with this information.

The accuracy checking section 33 may determine the degree of accuracy not just by comparing the maximum and minimum values with each other but also by reference to the relationship on the time axis between the points in time when the maximum and minimum values are found and the maximum and minimum value finding periods. Specifically, if the points in time when the maximum and minimum values are found coincide with the start or end times of the maximum and minimum value finding periods, then the greatest thickness difference, strain or elastic property may be regarded as having low accuracies. If the thickness variation waveform has inverted positive and negative values as shown in FIG. 12, then the thickness variation waveform has no local maximum values within the maximum value finding period. Thus, the maximum value during the maximum value finding period is obtained at either the start time or the end time of the maximum value finding period. In the same way, the thickness variation waveform has no local minimum values within the minimum value finding period, either, and therefore, the minimum value during the minimum value finding period is obtained at either the start time or the end time of the minimum value finding period. That is why the accuracy can also be checked properly based on such relationships.

If the accuracy is checked based on this criterion, it is sufficient to check the relationship between the point in time when at least one of the maximum and minimum values is found and its associated period on the time axis. This is because if one of the maximum and minimum values is not a correct value, then the greatest thickness difference, strain or elastic property will not be a correct value, either.

The accuracy checking section 33 may check the accuracy by either of these two methods or by using these two methods in combination. By combining a plurality of accuracy checking methods with each other, accuracy information with finer step widths can be obtained effectively.

FIGS. 13A and 13B show an example in which the greatest thickness difference, strain or elastic property is presented on the display section 21 so as to reflect the degree of accuracy that has been determined by the accuracy checking section 33. More specifically, FIG. 13A shows an exemplary image presented in a situation where the greatest thickness difference, strain or elastic property, of which the accuracy has been determined to be low, is set to a predetermined value. In the spatial distribution image $F_k$ shown in FIG. 13A, the image data items $f(k)_{34}$ and $f(k)_{44}$ have been regarded as having low accuracies and are set to a predetermined value. That is why these data items are presented in a different color from the other image data items. As described above, the accuracy checking section 33 may generate information showing the degree of accuracy and may present the spatial distribution image $F_k$ shown in FIG. 13A in accordance with the information generated.

Meanwhile, FIG. 13B shows an example in which a two-dimensional spatial distribution image $F_k$ showing the greatest thickness difference, strain or elastic property and another two-dimensional spatial distribution image $G_k$ showing the degree of accuracy are presented on the screen 70 at the same time. In FIG. 13B, the image data items $f(k)_{34}$ and $f(k)_{44}$ are presented in a predetermined gray-scale tone and the spatial distribution image $G_k$ shows that the accuracies are low in these areas.

By displaying these images, low-accuracy areas can be easily spotted on the screen on which the greatest thickness difference, strain or elastic property is presented, and the diagnosis can be carried out more accurately based on the results of measurements.

The greatest thickness difference and elastic property of a portion of a carotid wall were measured with this ultrasonic diagnostic apparatus 11. The results are as follows.

FIG. 14 shows the variation in the thickness of the anterior wall of a human carotid artery, which was measured with the ultrasonic diagnostic apparatus 11. The person under test was a 41-year-old man and the variation was measured for a partial period of one cardiac cycle (of about 700 ms) using the R wave of his electrocardiogram as a trigger signal. In FIG. 14, the greatest thickness difference in one cardiac cycle was 1.87+2.62=4.49 µm. In this case, the maximum thickness at the measuring point was 160 µm and the person under test had a blood pressure difference of 40 mmHg (=5.33 kPa). Consequently, the elastic property E was 5.33×160/4.24=190 kPa.

However, these maximum and minimum values were respectively obtained at about 100 ms and at about 545 ms in one cardiac cycle as shown in FIG. 14. As can be seen clearly if the results shown in FIG. 14 are compared with graph 8b of FIG. 8, the thickness difference resulting in these maximum and minimum values is an impossible behavior as a variation in the thickness of a vascular wall and is believed to have been caused by noise. In this manner, when the maximum and minimum thickness variations are obtained all through one cardiac cycle, those values may sometimes be affected by noise and inaccurate elastic property may be obtained.

FIG. 15 shows the variation in the thickness of the anterior wall of the same human carotid artery as that of FIG. 14. As shown in FIG. 15, if the period for finding the maximum thickness variation is changed so as to begin at 50 ms and end at 150 ms and if the period for finding the minimum thickness variation is changed so as to begin at 300 ms and end at 400 ms, then highly accurate maximum and minimum values can be selected. In that case, the greatest thickness difference was 1.87+1.25=3.12 µm. The maximum thickness at the measuring point was 160 µm and the person under test had a blood pressure difference of 5.33 kPa. Consequently, the elastic property E was 5.33×160/3.12=270 kPa. As a result, more accurate elastic property can be obtained. Besides, it can also be seen that the unwanted effects of spike noise generated at around 200 ms can be avoided by providing the maximum value find period and the minimum value finding period separately as shown in FIG. 15.

By changing the measuring period, the data acquisition period can be shortened to about a half, and therefore, the memory for storing the data acquired can have smaller capacity and the computer needs to do computations of reduced complexity per cardiac cycle. Consequently, the memory to be built in the ultrasonic diagnostic apparatus can have a reduced capacity and the elastic property can be figured out faster. Optionally, a computer with low computation performance may also be adopted since the computational complexity has been reduced. Then, the cost of the ultrasonic diagnostic apparatus can be cut down.

As described above, the ultrasonic diagnostic apparatus of this preferred embodiment finds the maximum and minimum thickness variations during two separately defined periods that are shorter than one cardiac cycle. Thus, the apparatus can obtain more accurate greatest thickness difference and elastic property with the influence of noise reduced.

Embodiment 2

Hereinafter, a second preferred embodiment of an ultrasonic diagnostic apparatus according to the present invention will be described. FIG. 16 is a block diagram showing the configuration of core sections of the ultrasonic diagnostic apparatus of the second preferred embodiment. Although not shown in FIG. 16, the ultrasonic diagnostic apparatus of the second preferred embodiment also includes the transmitting section 14, receiving section 15, time delay control section 16, phase detecting section 17, filter section and control section 30 as in the first preferred embodiment. All of these sections operate just as already described for the first preferred embodiment.

The ultrasonic diagnostic apparatus of this preferred embodiment also finds the maximum and minimum values of the thickness variations either during one cardiac cycle or during respective partial periods of one cardiac cycle and checks the degrees of accuracy of the greatest thickness difference, strain and elastic property based on the maximum and minimum values obtained. For that purpose, the computing section 19 includes the positional displacement calculating section 31a, the thickness variation calculating section 31b, a maximum/minimum value calculating section 31c', the attribute property value calculating section 32 and an accuracy checking section 33'. The positional displacement calculating section 31a and thickness variation calculating section 31b get their calculations done as in the first preferred embodiment described above. Also, the calculations are done by the maximum/minimum value calculating section 31c' as in the first preferred embodiment except that the maximum and minimum values of the thickness variations are obtained during different periods.

As already described in detail for the first preferred embodiment, the thickness variations are synchronous with one cardiac cycle and the maximum and minimum values of the thickness variations during one cardiac cycle are related to various events occurring at the heart during one cardiac cycle. That is why the maximum and minimum values can be determined during respective partial periods of one cardiac cycle associated with the thickness variations.

As is clear from the graphs 8b and 8f shown in FIG. 8, if the partial periods include periods in which the S and P waves of a pulse wave are observed, the maximum and minimum values are obtained correctly. In this preferred embodiment, the period for finding the maximum and minimum values is set as a continuous partial period of one cardiac cycle.

By shortening the period to find the maximum and minimum values, noise is less likely recognized as a maximum or minimum value by mistake. For example, if measurements are done during only the ejection period of one cardiac cycle, the ejection period accounts for approximately 30% of the entire cardiac cycle and the chances of noise interference can be reduced to about one-third. In addition, by shortening the measuring period, the complexity of computations to be done on the measured values can also be cut down. As a result, the manufacturing costs of the ultrasonic diagnostic apparatus can be reduced since there is no need to introduce a lot of memories into the ultrasonic diagnostic apparatus or use a high-performance computer with high computational processing ability. Or an ultrasonic diagnostic apparatus that can get measuring done at high speeds is realized.

As already described for the first preferred embodiment with reference to FIG. 8, the times when the S and P waves of the pulse wave are monitored and the times when the maximum and minimum thickness variations b1 and b2 are obtained can be set easily by using the biomedical signal. For example, if the electrocardiograph 22 is used as biomedical signal detecting means, then the data acquisition period may be defined to last from R wave through T wave. As a result, the maximum and minimum thickness variations can be obtained effectively. Optionally, the R wave may be replaced with P wave, Q wave or S wave, or the data acquisition period may be defined as a period lasting 0.5 second after the R wave was detected or lasting an amount of time corresponding to 40% of one cardiac cycle since the R wave was detected. Even so, similar effects are also achieved.

Alternatively, if a phonocardiograph is used as biomedical signal detecting means, then the data acquisition period may be defined so as to last from I sound through II sound to obtain the maximum and minimum thickness variations effectively. Optionally, the I sound may be replaced with IV sound or the II sound may be replaced with III sound. Alternatively, the data acquisition period may be defined to last 0.5 second from the I sound or to begin earlier than the I sound by an amount of time corresponding to 10% of one cardiac cycle and to end later than the I sound by an amount of time corresponding to 30% of one cardiac cycle. Even so, similar effects are also achieved.

As another alternative, if a pulse monitor is used as another biomedical signal detecting means, then the data acquisition period may be defined so as to last from S wave through C wave to obtain the maximum and minimum thickness variations effectively. Optionally, the C wave may be replaced with T wave or D wave. Alternatively, the data acquisition period may be defined as a period lasting 0.5 second from the S wave or a period beginning earlier than the S wave by an amount of time corresponding to 10% of one cardiac cycle and ending later than the S wave by an amount of time corresponding to 30% of one cardiac cycle.

Furthermore, instead of providing a separate instrument for detecting the biomedical signal outside of the ultrasonic diagnostic apparatus 11, the numerical values measured by the ultrasonic diagnostic apparatus 11 may also be used as a trigger signal. As shown in graph 8a of FIG. 8, there are local maximum and minimum points such as the points a1, a2 and a3, where the magnitude of positional displacement changes uniquely, in the curve representing the magnitudes of positional displacements at arbitrary points on the carotid artery under measurement. That is why even if those points a1, a2 and a3 are extracted by the computing section 19, the periods for finding the maximum and minimum thickness variations can also be defined within one cardiac cycle. It should be noted that the point a1 is an event resulting from a point with the lowest blood pressure at the measuring point on the blood vessel 3, the point a2 is an event resulting from a point with the highest blood pressure at the measuring point on the blood vessel 3, and the point a3 is an event resulting from a dichrotic notch.

If the measuring period is defined based on the magnitudes of positional displacement, the maximum and minimum thickness variations can be easily obtained by setting the data acquisition period from the point a1 through the point a3, for example. Alternatively, the point a3 may be replaced with the point a2. As another alternative, the data acquisition period may also be defined as lasting 0.5 second from the point a1 or beginning earlier than the point a1 by an amount of time corresponding to 10% of one cardiac cycle and ending later than the point a2 by the same amount of time.

Optionally, as shown in graph 8c, the points c1, c2 and c3 may be extracted from the curve representing the variation in the inside diameter of the blood vessel and used for defining the measuring periods. Or the points b1, b2 and b3 may be extracted from the curve representing the thickness variation shown in graph 8b and used for setting the measuring periods.

Using the biomedical signal generated by the biomedical signal detecting means, the electrocardiogram obtained by the electrocardiograph 22 may be input to the computing section 19 as shown in FIGS. 1 and 2. If the R wave is detected, the thickness variation may be calculated. But if the T wave is detected, then the calculation may be stopped as described above. The R and T waves may be detected by making the computing section 19 use the amplitude of the electrocardiogram, values obtained by differentiating the electrocardiogram, and their timings of appearance. Alternatively, the electrocardiograph 22 may also detect the R and T waves and may output a control signal to the computing section 19 on detecting those waves.

Also, if the timing of a specific signal such as a waveform that triggers the biomedical signal is close to the timing at which the maximum or minimum thickness variation is obtained or if a specific signal that rises after the maximum or minimum thickness variation is reached is used as a trigger, then the signal may be used as a trigger in the measuring period of the next cardiac cycle that follows the period in which the specific signal was obtained as a trigger.

As described above, the variation in thickness is obtained as a difference in the magnitude of positional displacement between two points defining the thickness. Accordingly, the maximum and minimum thickness variations may be derived from the magnitudes of positional displacement between two points during the period in which the maximum and minimum thickness variations should be obtained. The ultrasonic diagnostic apparatus 11 may obtain the maximum and minimum thickness variations by measuring the magnitudes of positional displacement all through one cardiac cycle (i.e., continuously) and extracting some of the magnitudes of positional displacement that fall within the period for obtaining the maximum and minimum thickness variations. Alternatively, the ultrasonic diagnostic apparatus 11 may also obtain the maximum and minimum thickness variations by measuring the magnitudes of positional displacement only within the particular period of one cardiac cycle (i.e., intermittently). The maximum and minimum thickness variations may be calculated either in real time during that period defined by the biomedical signal, for example, or during some period that does not agree with that period.

Considering the individual differences among persons under test, the measuring period for obtaining the maximum and minimum thickness variations preferably has a length corresponding to 5% through 75% of one cardiac cycle. The reasons are as follows. Specifically, if the measuring period were shorter than 5% of one cardiac cycle, then at least one of the maximum and minimum thickness variations could not be obtained. However, if the measuring period were longer than 75% of one cardiac cycle, then the effects to be achieved by shortening the measuring period could not be achieved fully and the measurement could be subjected to noise more easily. For these reasons, the measuring period, defined by using the biomedical signal as a trigger, preferably falls within this range. By setting the measuring period within this range, the computational complexity and the influence of noise would be reduced by approximately 25% to 95%.

Also, while diagnosed by the ultrasonic diagnostic apparatus, the organism is laid to rest and is likely to have little variation in cardiac cycle. That is why the measuring period does not have to be defined every cardiac cycle. Alternatively, once defined in accordance with the biomedical information described above, the measuring period may be repeated at the same intervals a number of times. Meanwhile, if the biomedical signal is detected every cardiac cycle and if the measuring period is defined based on that biomedical signal, then the elastic property can be evaluated just as intended even when the organism has an irregular cardiac cycle due to arrhythmia, for example.

In the preferred embodiment described above, the measuring period is supposed to be set with the specific signal obtained by only one type of biomedical signal detecting section. Optionally, the measuring period may also be defined by specific signal obtained by a plurality of biomedical signal detecting sections. For example, the R wave of the electrocardiogram may be used as a signal that defines the beginning of a measuring period and the point c3 of the variation in the inside diameter of the blood vessel may be used as a signal that defines the end of the measuring period.

Also, in the preferred embodiment described above, the greatest thickness difference is obtained by finding the maximum and minimum thickness variations. Alternatively, the thicknesses themselves may be measured and the greatest thickness difference may be obtained from the maximum and minimum thicknesses. Suppose the thickness variation is already known. In that case, if the thickness when the thickness variation starts to be measured is known, then the variation in thickness with time can be obtained as the sum of the thickness at the start of measuring and the thickness variation. The thickness at the start of measuring is nothing but the initial value of the distance between two arbitrary points to calculate the magnitudes of positional displacement for, and is a known parameter for the ultrasonic diagnostic apparatus 11 of this preferred embodiment.

Next, the accuracy checking section 33' will be described. The accuracy checking section 33' checks the degree of accuracy of at least one of the greatest thickness difference, strain and elastic property based on the maximum and minimum values that have been figured out by the maximum/minimum value calculating section 31c'. More specifically, the accuracy checking section 33' compares the points in time when the maximum and minimum values are found with each other, and determines the degree of accuracy based on the result of the comparison.

FIG. 17 shows a part of a thickness variation waveform corresponding to one cardiac cycle in a situation where one cardiac cycle is defined synchronously with the beginning of a systolic phase. A partial period for finding the maximum and minimum values during one cardiac cycle is defined as a first period. In the first period, the maximum value $D(t_{max})$ is found at a time $t_{max}$ and the minimum value $D(t_{min})$ is found at a time $t_{min}$. At a normal thickness variation $D(t)$, if the measuring period is set as shown in FIG. 17, the maximum value is observed earlier than the minimum value. Thus, the times $t_{max}$ and $t_{min}$ satisfy the inequality $t_{max} < t_{min}$ and the accuracy checking section 33' regards the greatest thickness difference, strain or elastic property, calculated based on these maximum and minimum values $D(t_{max})$ and $D(t_{min})$, as having high accuracy.

On the other hand, the ultrasonic reflected wave may have an extremely small amplitude or include some noise. In that case, the magnitude of positional displacement calculated by using a signal representing the wave that has been reflected from such a spot may have an inaccurate value. Specifically, its waveform may have an excessively large waveform or an excessively small waveform overall. In such a situation, the thickness variation waveform obtained based on those magnitudes of positional displacements will have inverted positive and negative values as shown in FIG. 18. The positive and negative values of the thickness variation waveform may also be inverted for the reason that has been described for the first preferred embodiment with reference to FIGS. 10A, 10B, 11A and 11B. If the maximum and minimum values are obtained in FIG. 18 as in FIG. 17, the maximum value $D'(t_{max}')$ is found at a time $t_{max}'$ and the minimum value $D'(t_{min}')$ is found at a time $t_{min}'$. In this case, the times $t_{max}'$ and $t_{min}'$ satisfy the inequality $t_{max}' > t_{min}'$ and the accuracy checking section 33' regards the greatest thickness difference, strain or elastic property, calculated based on these maximum and minimum values $D'(t_{max}')$ and $D'(t_{min}')$, as having low accuracy.

When determining, based on the maximum and minimum values, that the greatest thickness difference, strain or elastic property has a low accuracy, the accuracy checking section 33' sets the greatest thickness difference, strain or elastic property to a predetermined value (e.g., zero or a negative value) as already described for the first preferred embodiment. Alternatively, the accuracy checking section 33' may generate information showing the degree of accuracy. The information showing the degree of accuracy is either "high accuracy" or "low accuracy". And the accuracy checking section 33' may generate an appropriate numerical value (consisting of zeros and ones, for example) in accordance with this information.

The greatest thickness difference, strain or elastic property is presented on the display section 21 so as to reflect the degree of accuracy that has been determined by the accuracy checking section 33'. If the greatest thickness difference, strain or elastic property, of which the accuracy has been determined to be low, is set to a predetermined value, a color (e.g., black) that is not used to present a normal greatest thickness difference or elastic property may also be displayed on the screen. Or the transparency on the screen may be changed according to the degree of accuracy. Furthermore, if the accuracy checking section 33' has generated information showing the degree of accuracy, then another two-dimensional map may be used exclusively for presenting the accuracy information and the accuracy may be presented according to a predefined color scheme. The specific display method may be the same as that already described for the first preferred embodiment.

In the accuracy checking section 33', the conditions for checking the accuracy according to the points in time when the maximum and minimum values are obtained depend on how to set one cardiac cycle in the thickness variation waveform. As shown in FIG. 19, the trigger point, marking the beginning of one cardiac cycle, may be set between b1 and b2 of the graph 8b shown in FIG. 8. That is to say, the start time of one cardiac cycle may be defined 0.1 second after the S wave of the electrocardiogram or the I sound of the phonocardiogram has been detected. In that case, the accuracy checking section 33' determines that the accuracy is high if the time $t_{max}$ when the maximum value $D(t_{max})$ is found and the time $t_{min}$ when the minimum value $D(t_{min})$ is found satisfy the inequality $t_{max} > t_{min}$.

Alternatively, the accuracy checking section 33' may also check the accuracy by another method. Specifically, as shown in FIG. 20, a first period for finding the maximum and minimum values may be defined as a partial period of one cardiac cycle and a period in which the maximum and minimum values are expected to appear may be further defined as a second period within the first period. The expected maximum/minimum value appearing period is set in view of the mechanism of the circulatory system and is preferably defined such that the maximum and minimum values appear at a probability of 99.9% within that period. Just like the maximum and minimum value finding periods, the expected maximum/minimum value appearing period may be set based on a biomedical signal such as an electrocardiogram or phonocardiogram or a waveform representing the magnitude of positional displacement.

The accuracy checking section 33' determines whether or not the points in time when the maximum and minimum values that have been figured out by the maximum/minimum value calculating section 31c' are found fall within the expected maximum/minimum value appearing period. If the answer is YES, the accuracy checking section 33' regards the greatest thickness difference, strain or elastic property, calculated based on the maximum and minimum values, as having high accuracy.

In the example shown in FIG. 20, the times $t_{max}$ and $t_{min}$, when the maximum and minimum values are found, respectively, both fall within the expected maximum/minimum value appearing period, and therefore, the accuracy checking section 33' judges the accuracy to be high.

If the thickness variation waveform includes noise and if the noise is measured as the minimum value $D''(t_{min}'')$ as shown in FIG. 21, then the time $t_{min}''$ is out of the expected maximum/minimum value appearing period. Consequently, the accuracy of the greatest thickness difference, strain or elastic property to be estimated based on the maximum value $D''(t_{max}'')$ and minimum value $D''(t_{min}'')$ is judged to be low.

It should be noted that the period in which the maximum and minimum values are highly likely to appear does not have to one continuous period. Alternatively, an expected maximum value appearing period in which the maximum value is highly likely to appear and an expected minimum value appearing period in which the minimum value is highly likely to appear may be defined separately within the first period as shown in FIG. 22. In that case, the accuracy checking section 33' determines whether or not the maximum value is found within the expected maximum value appearing period and whether or not the minimum value is found within the expected minimum value appearing period.

Optionally, the accuracy checking methods described above may be combined with each other. Then, even more precise accuracy information can be acquired. For example, if the thickness variation waveform shown in FIG. 21 is obtained, the accuracy is judged to be high because $t_{max}'' < t_{min}''$ is satisfied just by comparing the respective times when the maximum and minimum values are found. However, the accuracy can be checked more appropriately by adopting the expected maximum and minimum value appearing periods.

As described above, the ultrasonic diagnostic apparatus of this preferred embodiment evaluates the reliability of the resultant greatest thickness difference, strain or elastic property by checking the accuracy by reference to the respective times when the maximum and minimum values of the thickness variations are found. Thus, the apparatus can make highly accurate and reliable diagnosis.

Embodiment 3

Hereinafter, an ultrasonic diagnostic apparatus according to a third preferred embodiment of the present invention will be described. FIG. 23 is a block diagram showing a configuration for the core sections of the ultrasonic diagnostic apparatus of this third preferred embodiment. Although not shown in FIG. 23, the ultrasonic diagnostic apparatus of the third preferred embodiment also includes the transmitting section 14, receiving section 15, time delay control section 16, phase detecting section 17, filter section 18 and control section 30 just like the counterpart of the first preferred embodiment. All of these sections operate just as already described for the first preferred embodiment.

The ultrasonic diagnostic apparatus of this preferred embodiment determines whether or not the greatest thickness difference, strain or elastic property, obtained every cardiac cycle, is a highly reliable one overall. For that purpose, the computing section 19 includes a shape measured value calculating section 31, an attribute property value calculating section 32 and a go/no-go testing section 33.

As already described in detail for the first preferred embodiment, the shape measured value calculating section 31 figures out the attribute property value. More specifically, the shape measured value calculating section 31 calculates the magnitudes of positional displacements at multiple measuring points that have been set within the tissue of an organism by using the real- and imaginary-part signals of a phase detected signal, and then obtains a variation in thickness between two arbitrary points based on those magnitudes of positional displacements. The attribute property value calculating section 32 figures out an attribute property value. More specifically, the attribute property value calculating section 32 calculates the strain or elastic property based on the difference between the maximum and minimum values of the thickness variations. As already described for the first and second preferred embodiments, the maximum and minimum values of the thickness variations may be found either within a partial period that has been defined in one cardiac cycle or within the maximum value and minimum value finding periods. By finding the maximum and minimum values within the partial period of one cardiac cycle, the measuring error due to the noise can be reduced as already described for the first and second preferred embodiments.

The go/no-go testing section 35 determines, for every single data, whether or not the greatest thickness difference calculated by the shape measured value calculating section 31 or the strain or elastic property calculated by the attribute property value calculating section 32 is a reliable value. For example, if the elastic property is obtained as a two-dimensional matrix consisting of six rows by five columns, the go/no-go testing section 35 determines whether the elastic property value at each position is reliable or not. Thus, the go/no-go testing section 35 makes the decisions on thirty points in total. The go/no-go test may be made as follows. For example, in a situation where the thickness variation is adopted as a parameter, if some data shows an increase in thickness that should have decreased with a rise in blood pressure, then the data may be regarded as a "no-go". Or if some data shows that the time when the thickness reaches its maximum value (or minimum value) and the time when the blood pressure value reaches its minimum value (or maximum value) exceed predetermined threshold values, then the data may be regarded as a "no-go", too.

The go/no-go testing section 35 calculates the go/no-go ratio for the respective positions under test. FIG. 24A shows an elastic property image in which go/no-go information has been added to the elastic property represented by six rows and five columns. The image display area is defined by specifying an ROI on the screen of the display section 21 as already described for the first preferred embodiment. In FIG. 24A, the no-go positions are shown in black, 18 out of 30 positions were judged "go", and the go ratio is 60%. Among the data shown in FIG. 24A, the data on the first row and the data on the sixth row were collected from outside of the vascular wall, thus not showing accurate coefficients of elasticity. Optionally, the go/no-go testing section 33 may calculate a no-go ratio instead of the go ratio.

FIG. 24B shows only a vascular wall portion extracted from the elastic property image shown in FIG. 24A. To extract a vascular wall area from a spatial distribution image, a difference in acoustic impedance may be used, for example. Alternatively, the ROI may be adjusted so as to consist of the vascular wall only. Among the 20 positions showing the vascular wall, 18 positions have "go" data and the go ratio is 90%. A method of controlling the display of an ultrasonic diagnostic apparatus based on the go ratio calculated in this manner will be described. The data to be judged "go" or "no-go" preferably covers only the area in which the elastic property should be evaluated. That is why the go/no-go tests are preferably carried out on the area shown in FIG. 24B rather than the area shown in FIG. 24A and the go ratio that has been figured out based on the test results is preferably used to control the display.

The go/no-go testing section 35 compares the go ratio calculated in this manner to the predetermined threshold value that is stored in the computed data storage section 20. If the go ratio is equal to or higher than the threshold value, the go/no-go testing section 35 outputs a presentation signal showing that the go/no-go ratio is good to the display section 21. In response to the presentation signal, the display section 21 presents image data. For example, if the threshold value is set to 80%, image data with a go ratio of 90% is presented on the display section 21. However, if the threshold value is 95%, then the image data will not be presented on the display section 21. On the other hand, when calculating a no-go ratio, the go/no-go testing section 35 outputs a presentation signal showing that the go/no-go ratio is good if the no-go ratio is equal to or lower than the threshold value. That is to say, the go/no-go testing section 35 generates a presentation signal when the go/no-go ratio and threshold value satisfy the predetermined conditions. The go/no-go testing section 35 performs such an operation every cardiac cycle of the given organism.

FIG. 25 is a flowchart showing an exemplary procedure of controlling the ultrasonic diagnostic apparatus using a go ratio. More specifically, a method of controlling the presentation of a spatial distribution image based on a result of comparison between the go ratio $a_n$ calculated by the go/no-go testing section 35 and the go ratio threshold value A that has been set in advance by the operator of the ultrasonic diagnostic apparatus is shown. The procedure to be described below may be stored as a program or firmware to be carried out by a computer on a ROM or any other storage medium provided for the ultrasonic diagnostic apparatus.

First, before making measurements, the operator sets the go ratio threshold value A on the ultrasonic diagnostic apparatus (in Step S1). Next, the operator operates the ultrasonic diagnostic apparatus to get the shape measured value or attribute property value (e.g., the elastic property) of a desired point calculated by the distribution image generating section 34 (in Step S2) and then get its spatial distribution image $F_1$ generated (in Step S3). Subsequently, the respective parts of the image are judged go or no-go and the go ratio $a_1$ is calculated (in Step S4) and compared to the threshold value A (in Step S5). If the go ratio $a_1$ is higher than the threshold value A, the spatial distribution image $F_1$ is presented on the display section 21 in response to the presentation signal supplied from the go/no-go testing section 33 (in Step S6) to complete the operation of this cardiac cycle. Then, the process goes back to Step S2 to carry out the processing steps S2 through S6 all over again. On the other hand, if the go ratio $a_1$ is lower than the threshold value A, then the operation of this cardiac cycle is completed without presenting the spatial distribution image $F_1$ and the process goes back to Step S2. If the previous spatial distribution image $F_o$ is presented on the display section 21, then that image is maintained.

In the example shown in FIG. 25, the processing step S3 of generating the distribution image and the processing step S4 of calculating the go ratio may be carried out in reverse order. FIG. 26 is a flowchart showing that situation.

Unlike the control method shown in FIG. 25, the spatial distribution image $F_n$ is generated in Step S15 only if it has been determined in Step S14 that the go ratio $a_n$ has exceeded the threshold value A according to the method shown in FIG. 26. That is to say, the control method shown in FIG. 26 is advantageous in that the distribution image generating section 34 needs to carry out computations a smaller number of times.

The go ratio $a_n$ may be shown on the display section 21 every time the user requests it. Even if the image F is not presented, the operator can see whether the go ratio of the measuring data is increasing or decreasing and can determine whether the measuring points or positions are appropriate or not by showing the go ratio for him or her.

If the operator wants to stop or finish the measurements, then he or she may input a freeze signal to the ultrasonic diagnostic apparatus. The freeze signal may be input in any of the processing steps shown in FIGS. 25 and 26. On sensing that the freeze signal has been input, the ultrasonic diagnostic apparatus stops all measurements. On the display section 21, presented is the last spatial distribution image F along with its associated go ratio $a_n$ among various images of which the go ratios $a_n$ are higher than the threshold value A.

To perform such an operation, not only the presentation of the spatial distribution image $F_n$ but also the storage of spatial distribution images $F_n$ and go ratios $a_n$, which exceed the threshold value A, on the computed data storage section 20 are preferably done in the processing steps S6 and S16 shown in FIGS. 25 and 26. If those images $F_n$ and go ratios $a_n$ are stored, then the operator can view only reliable images that exceed the threshold value A after the freeze signal has been input, and therefore, can make a diagnosis efficiently. In addition, if the freeze signal has been input, an image F with the highest go ratio in the period between the beginning of the measurement and the input of the freeze signal can be read out from the computed data storage section 20 and presented on the display section 21. Optionally, the control operation may also be performed such that not all measurements are stopped immediately but only the presented one is continued even when the freeze signal is input.

FIG. 27 is a graph showing the go ratios $a_n$ that were calculated by the ultrasonic diagnostic apparatus of this preferred embodiment every cardiac cycle. The abscissa represents the number of times the spatial distribution images have been generated since the measurements were started, i.e., the number of cardiac cycles since the beginning of the measurements. The threshold value A was set to 90%. The go ratio $a_n$ was low for a while after the measurements were started because the position or respiratory state of the person under test or the operator holding the ultrasonic probe was still not fixed. But the go ratio $a_n$ increased gradually. As indicated by the encircled numbers on the axis of abscissas shown in FIG. 27, the go ratios $a_n$ of the fifth to eighth cycles and the tenth cycle are higher than the threshold value A. The ultrasonic diagnostic apparatus presents the spatial distribution image on the display section 21 when the go ratio $a_n$ is higher than the threshold value A. Specifically, no spatial distribution images are presented on the display section 21 from the beginning of the measurements through the fourth cardiac cycle. And a spatial distribution image $F_5$ is presented for the first time in the fifth cardiac cycle. Thereafter, an updated spatial distribution image is presented every cardiac cycle through the eighth cardiac cycle. The go ratio $a_n$ of the ninth cardiac cycle is lower than the threshold value A. Thus, in the ninth cardiac cycle, the spatial distribution image is not updated but the previous one $F_8$ is presented continuously.

After that, the image is updated again into the spatial distribution image $F_{10}$ in the tenth cycle.

As described above, according to this preferred embodiment, the go ratio a calculated by the go/no-go testing section 33 is compared to the threshold value A that has been set in advance by the operator and a spatial distribution image F is presented only when the go ratio a is higher than the threshold value A. Thus, the operator can selectively view only results of measurements that surpass a certain level of reliability and can make an even more accurate diagnosis.

Optionally, the end of the measurements may be controlled by using the go ratio $a_n$. For example, a value showing that the results of measurements have sufficient reliability may be set as the threshold value A' and it is determined whether the go ratio $a_n$ is higher than the threshold value A' or not. If the answer is YES, the measurements are finished and the last spatial distribution image is either printed out or stored on a storage medium. This control technique may be combined with the method of controlling the presentation of the spatial distribution image described above. If the spatial distribution image is also presented, then the threshold value A' for use to control the end of the measurements preferably shows higher degree of reliability than the threshold value A for use to present the spatial distribution image. Then, the measurements can be finished automatically and a desired spatial distribution image can be generated when the reliability of measurements reaches a sufficiently high level after the measurements were started.

In the preferred embodiment described above, the two-dimensional distribution of the elastic property of a vascular wall is figured out. Alternatively, the ultrasonic diagnostic apparatus of the present invention is also effectively applicable for use in other circulatory organs such as heart and in liver, mamma and other body tissues.

Also, the preferred embodiment described above is an ultrasonic diagnostic apparatus that figures out the two-dimensional distribution of shape measured values or attribute property values and presents it as an image every cardiac cycle. Alternatively, a three-dimensional distribution of shape measured values or attribute property values may be figured out by using a 3D mechanical probe, for example, and presented as an image every cardiac cycle.

Furthermore, in the preferred embodiment described above, the go ratio and the threshold value are compared to each other and the display section 21 is controlled based on the result of the comparison. That is why in the initial stages of measurements done by the ultrasonic diagnostic apparatus, the measuring states are still inconstant, and therefore, the go ratio may rarely exceed the threshold value and the images may not be presented so often. In that case, the presentation may be controlled by using the go ratio itself as a reference. Then, the images can also be presented even in the initial stages of measurements.

Specifically, the computed data storage section 20 stores the go/no-go ratios and the shape measured values and/or the attribute property values. Every time calculated a go/no-go ratio, the go/no-go testing section 35 compares it to the best go/no-go ratio that is stored in the computed data storage section 20. If the go/no-go ratio is higher than the best value, then the go/no-go testing section 35 generates a presentation signal. The computed data storage section 20 may store all go/no-go ratios, shape measured values and attribute property values such that the best go/no-go ratio and its associated shape measured value and attribute property value can be detected among those go/no-go ratios stored. Alternatively, the computed data storage section 20 may store only the best go/no-go ratio and its associated shape measured value and attribute property value while always updating them.

FIG. 28 is a flowchart showing an exemplary procedure of controlling the ultrasonic diagnostic apparatus based on the go ratio $a_n$. The go ratio $a_n$ may be calculated just as described above. The go ratio $a_n$ calculated by the go/no-go testing section 33 and the best go ratio $a_{best}$ during the period that has been defined in advance by the operator of the ultrasonic diagnostic apparatus are compared to each other. And the presentation of the spatial distribution image $F_n$ is controlled based on the result of the comparison.

First, the operator operates the ultrasonic diagnostic apparatus to get the shape measured value or attribute property value (e.g., the elastic property) of a desired point calculated by the distribution image generating section 34 (in Step S21). Next, the spatial distribution image $F_1$ of the elastic property measured and the go ratio $a_1$ of the image $F_1$ are figured out and presented on the display section 21 (in Step S22). The go/no-go testing section 33 gets the image $F_1$ and go ratio $a_1$ stored as currently best values $F_{best}$ and $a_{best}$ on the computed data storage section 20 (in Step S23).

In the next cardiac cycle, the distribution image generating section 34 measures the elastic property (in Step S24) and figures out a distribution image $F_2$ (in Step S25). Subsequently, the respective parts of the image are judged go or no-go and a go ratio $a_2$ is calculated (in Step S26) and then compared to the best go ratio $a_{best}$ (in Step S27). If the go ratio $a_2$ is higher than the best go ratio $a_{best}$, then the image $F_2$ and go ratio $a_2$ are stored as updated $F_{best}$ and $a_{best}$, respectively, (in Step S28) and the spatial distribution image $F_2$ is presented on the display section 21 (in Step S29) to complete the operation of this cardiac cycle. Then, the process goes back to Step S24 to carry out the processing steps S24 through S29 all over again. On the other hand, if the go ratio $a_2$ is lower than the best go ratio $a_{best}$, then the operation of this cardiac cycle is completed without presenting the spatial distribution image $F_2$ and the process goes back to Step S24.

If the operator wants to stop or finish the measurements, then he or she may input a freeze signal to the ultrasonic diagnostic apparatus. The freeze signal may be input in any of the processing steps shown in FIG. 28. On sensing that the freeze signal has been input, the ultrasonic diagnostic apparatus stops all measurements. On the display section 21, presented are the best go ratio $a_{best}$ and spatial distribution image $F_{best}$. Optionally, the control operation may also be performed such that not all measurements are stopped immediately but only the presented one is continued even when the freeze signal is input.

FIG. 29 is a graph showing the go ratios $a_n$ that were calculated by the ultrasonic diagnostic apparatus of this preferred embodiment every cardiac cycle. As in FIG. 27, the abscissa represents the number of times the spatial distribution frames have been generated since the measurements were started, i.e., the number of cardiac cycles since the beginning of the measurements. The go ratio $a_n$ was low for a while after the measurements were started because the position or respiratory state of the person under test or the operator holding the ultrasonic probe 13 was still not fixed. But the go ratio $a_n$ increased gradually. In the cardiac cycles indicated by the encircled numbers on the axis of abscissas shown in FIG. 29, the best values $F_{best}$ and $a_{best}$ were updated, and therefore, updated spatial distribution images were presented. That is to say, right after the measurements have been started, the go ratio $a_n$ goes on increasing one cardiac cycle after another and the spatial distribution image is updated every cardiac cycle. The measurements will get settled soon and the go ratio $a_n$ will become substantially constant. Then, the spatial distribution image is updated only if the go ratio $a_n$ shows an even higher degree of reliability of measurements.

As described above, according to this preferred embodiment, right after the measurements have been started, an updated spatial distribution image is presented frequently. However, when the measurements get settled, the spatial distribution image showing the highest level of reliability is maintained. That is why as the measurements get settled, the image presented on the display section becomes easier to view and the operator can selectively view only results of measurements that surpass a certain level of reliability. As a result, he or she can make an even more accurate diagnosis.

INDUSTRIAL APPLICABILITY

The ultrasonic diagnostic apparatus of the present invention can be used effectively to evaluate the attribute and shape properties of a vital tissue, and the elastic property thereof, in particular. Among other things, the apparatus can be used particularly effectively to detect or prevent the disease of arterial sclerosis by measuring the elastic property of a vascular wall.

The invention claimed is:

1. An ultrasonic diagnostic apparatus for use with an ultrasonic probe, the ultrasonic diagnostic apparatus comprising:
a transmitting section for driving the ultrasonic probe that sends out an ultrasonic transmitted wave toward a tissue of an organism;
a receiving section configured to receive an ultrasonic reflected wave through the ultrasonic probe to generate a received signal, the ultrasonic reflected wave being produced by getting the ultrasonic transmitted wave reflected by the tissue of the organism;
a phase detecting section configured to detect the phase of the received signal to generate a phase detected signal;
a positional displacement calculating section configured to calculate magnitudes of positional displacements at multiple measuring points within the tissue, which have been set within the tissue of the organism, based on the phase detected signal;
a thickness variation calculating section configured to calculate thicknesses or thickness variations based on the magnitudes of positional displacements, each said thickness or each said thickness variation being measured between two arbitrary points within the tissue, which have been set with respect to the multiple measuring points; and
a maximum/minimum value calculating section configured to find the maximum and minimum thicknesses or the maximum and minimum thickness variations during a maximum value finding period and a minimum value finding period, which are defined as different partial periods of one cardiac cycle of the organism, wherein a sum of the maximum and minimum value finding periods is less than one a cardiac cycle,
wherein at least one of the greatest thickness difference, strain and elastic property during one cardiac cycle is calculated based on either a difference between the maximum and minimum thicknesses or a difference between the maximum and minimum thickness variations.

2. The ultrasonic diagnostic apparatus of claim 1, further comprising an attribute property value calculating section that receives information about the maximum and minimum thicknesses or the maximum and minimum thickness variations and information about a blood pressure value of the organism and that figures out an elastic property based on either the difference between the maximum and minimum thicknesses or the difference between the maximum and minimum thickness variations and on the blood pressure value.

3. The ultrasonic diagnostic apparatus of claim 1, wherein the maximum/minimum value calculating section sets the maximum value finding period and the minimum value finding period during the one cardiac cycle of the organism so as not to overlap with each other.

4. The ultrasonic diagnostic apparatus of claim 1, wherein the maximum/minimum value calculating section sets at least one of the maximum value finding period and the minimum value finding period synchronously with a biomedical signal generated by the organism.

5. The ultrasonic diagnostic apparatus of claim 4, wherein the biomedical signal is represented as an electrocardiogram by an electrocardiograph.

6. The ultrasonic diagnostic apparatus of claim 5, wherein at least one of the maximum value finding period and the minimum value finding period is set based on at least one of P, Q, R, S, T and U waves of the electrocardiogram.

7. The ultrasonic diagnostic apparatus of claim 4, wherein the biomedical signal is represented as a phonocardiogram by a phonocardiograph.

8. The ultrasonic diagnostic apparatus of claim 7, wherein at least one of the maximum value finding period and the minimum value finding period is set based on at least one of I, II, III and IV sounds of the phonocardiogram.

9. The ultrasonic diagnostic apparatus of claim 4, wherein the biomedical signal is a sphygmogram.

10. The ultrasonic diagnostic apparatus of claim 9, wherein at least one of the maximum value finding period and the minimum value finding period is set based on at least one of S, P, T, C and D waves of the sphygmogram.

11. The ultrasonic diagnostic apparatus of claim 1, wherein the maximum/minimum value calculating section sets at least one of the maximum value finding period and the minimum value finding period based on a positional displacement waveform that has been figured out by the positional displacement calculating section prior to the setting of the maximum value finding period and the minimum value finding period.

12. The ultrasonic diagnostic apparatus of claim 1, wherein the thickness variation calculating section figures out a thickness variation waveform prior to the setting of the maximum value finding period and the minimum value finding period, the thickness variation waveform showing a variation in the thickness of the body tissue, according to the magnitude of positional displacement and wherein at least one of the maximum value finding period and the minimum value finding period is set based on the thickness variation waveform.

13. The ultrasonic diagnostic apparatus of claim 1, wherein the thickness variation calculating section figures out a vascular caliber variation waveform prior to the setting of the maximum value finding period and the minimum value finding period, the vascular caliber waveform showing a variation in the vascular caliber of the body tissue, according to the magnitude of positional displacement and wherein at least one of the maximum value finding period and the minimum value finding period is set based on the vascular caliber variation waveform.

14. The ultrasonic diagnostic apparatus of claim 1, wherein each of the maximum value finding period and the minimum value finding period has a length corresponding to 1% to 25% of one cardiac cycle.

15. The ultrasonic diagnostic apparatus of claim 1, further comprising an accuracy checking section for checking an accuracy of at least one of the greatest thickness difference, the strain and the elastic property based on a result of comparison between the maximum and minimum thicknesses or between the maximum and minimum thickness variations.

16. The ultrasonic diagnostic apparatus of claim 15, wherein if the maximum value is equal to or smaller than the minimum value, then the accuracy checking section judges the accuracy of at least one of the greatest thickness difference, the strain and the elastic property to be low.

17. The ultrasonic diagnostic apparatus of claim 1, further comprising an accuracy checking section for checking the accuracy of at least one of the greatest thickness difference, the strain and the elastic property based on a relation between a time when at least one of the maximum and minimum thicknesses or the maximum and minimum thickness variations is obtained and at least one of the associated maximum and minimum value finding periods.

18. The ultrasonic diagnostic apparatus of claim 17, wherein if the time when at least one of the maximum and minimum thicknesses or the maximum and minimum thickness variations is obtained coincides with a start time or end time of its associated finding period, then the accuracy of at least one of the greatest thickness difference, the strain and the elastic property is judged low.

19. The ultrasonic diagnostic apparatus of claim 15, wherein the maximum/minimum value calculating section or the attribute property value calculating section sets at least one of the greatest thickness difference, the strain and the elastic property equal to a predetermined value according to the accuracy.

20. The ultrasonic diagnostic apparatus of claim 15, wherein the accuracy checking section generates information showing the degree of the accuracy.

21. The ultrasonic diagnostic apparatus of claim 19, further comprising a display section for presenting at least one of the greatest thickness difference, the strain and the elastic property.

22. The ultrasonic diagnostic apparatus of claim 20, further comprising a display section for presenting at least one of the greatest thickness difference, the strain and the elastic property, which is displayed two-dimensionally according to a position on the tissue of the organism in accordance with the information showing the degree of the accuracy.

23. The ultrasonic diagnostic apparatus of claim 20, further comprising a display section for presenting at least one of the greatest thickness difference, the strain and the elastic property and the accuracy, represented by the information showing the degree of the accuracy, as two-dimensional images reflecting the position on the tissue of the organism.

24. A method for getting an ultrasonic diagnostic apparatus controlled by a control section of the ultrasonic diagnostic apparatus, the method comprising the steps of:
(A) sending out an ultrasonic transmitted wave and receiving an ultrasonic reflected wave through an ultrasonic probe to generate a received signal, the ultrasonic reflected wave being produced by getting the ultrasonic transmitted wave reflected by a tissue of an organism;
(B) detecting a phase of the received signal to generate a phase detected signal;
(C) calculating magnitudes of positional displacements at multiple measuring points within the tissue, which have been set within the tissue of the organism, based on the phase detected signal;
(D) calculating thicknesses or thickness variations based on the magnitudes of positional displacements, each said thickness or each said thickness variation being measured between two arbitrary points within the tissue that have been set with respect to the multiple measuring points;
(E) finding either the maximum and minimum thicknesses or the maximum and minimum thickness variations during a maximum value finding period and a minimum value finding period, which are defined as different partial periods of one cardiac cycle of the organism, wherein a sum of the maximum and minimum value finding periods is less than one a cardiac cycle; and
(F) calculating at least one of the greatest thickness difference, strain and elastic property based on either a difference between the maximum and minimum thicknesses or a difference between the maximum and minimum thickness variations.

25. The method of claim 24, wherein the step (F) includes receiving information about the maximum and minimum thicknesses or the maximum and minimum thickness variations and information about a blood pressure value of the organism and figuring out an elastic property based on either the difference between the maximum and minimum thicknesses or the difference between the maximum and minimum thickness variations and on the blood pressure value.

26. The method of claim 24, wherein the step (E) includes setting the maximum value finding period and the minimum value finding period during the one cardiac cycle of the organism such that the maximum and minimum value finding periods do not overlap with each other.

27. The method of claim 24, wherein the step (E) includes setting at least one of the maximum value finding period and the minimum value finding period synchronously with a biomedical signal generated by the organism.

28. The method of claim 27, wherein the step (E) includes representing the biomedical signal as an electrocardiogram by an electrocardiograph.

29. The method of claim 24, further comprising the step (G1) of checking an accuracy of at least one of the greatest thickness difference, the strain and the elastic property based on a result of comparison between the maximum and minimum thicknesses or between the maximum and minimum thickness variations.

30. The method of claim 29, wherein if the maximum value is equal to or smaller than the minimum value, then the step (G1) includes judging the accuracy of at least one of the greatest thickness difference, the strain and the elastic property to be low.

31. The method of claim 24, further comprising the step (G2) of checking the accuracy of at least one of the greatest thickness difference, the strain and the elastic property based on a relation between a time when at least one of the maximum and minimum thicknesses or the maximum and minimum thickness variations is obtained and at least one of the associated maximum and minimum value finding periods.

32. The method of claim 31, wherein if the time when at least one of the maximum and minimum thicknesses or the maximum and minimum thickness variations is obtained coincides with a start time or end time of its associated finding period, then the step (G2) includes judging the accuracy of at least one of the greatest thickness difference, the strain and the elastic property to be low.

33. The method of claim 29, further comprising the step (H) of setting at least one of the greatest thickness difference, the strain and the elastic property equal to a predetermined value according to the accuracy.

34. The method of claim 29, wherein the step (G2) includes generating information showing the degree of the accuracy.

35. The method of claim 33, further comprising the step (11) of presenting at least one of the greatest thickness difference, the strain and the elastic property.

36. The method of claim 34, further comprising the step (12) of presenting at least one of the greatest thickness difference, the strain and the elastic property, which is displayed two-dimensionally according to a position on the tissue of the organism in accordance with the information showing the degree of the accuracy.

37. The method of claim 34, further comprising the step (13) of presenting at least one of the greatest thickness difference, the strain and the elastic property and the accuracy, represented by the information showing the degree of the accuracy, as two-dimensional images reflecting the position on the tissue of the organism.

* * * * *